(12) United States Patent
Oldfield et al.

(10) Patent No.: US 7,371,225 B2
(45) Date of Patent: May 13, 2008

(54) METHOD FOR CONVECTION ENHANCED DELIVERY OF THERAPEUTIC AGENTS

(75) Inventors: Edward H. Oldfield, Philomont, VA (US); Russel R. Lonser, Silver Spring, MD (US); Kayhan Garmestani, Potomac, MD (US); Martin W. Brechbiel, Annandale, VA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 257 days.

(21) Appl. No.: 10/528,310

(22) PCT Filed: Sep. 24, 2003

(86) PCT No.: PCT/US03/30155

§ 371 (c)(1),
(2), (4) Date: Mar. 17, 2005

(87) PCT Pub. No.: WO2004/031348

PCT Pub. Date: Apr. 15, 2004

(65) Prior Publication Data

US 2006/0073101 A1 Apr. 6, 2006

Related U.S. Application Data

(60) Provisional application No. 60/413,673, filed on Sep. 24, 2002.

(51) Int. Cl.
*A61M 31/00* (2006.01)
(52) U.S. Cl. ........................................................ 604/49
(58) Field of Classification Search ................... 604/49; A61M 31/00
See application file for complete search history.

(56) References Cited

U.S. PATENT DOCUMENTS

| | | | |
|---|---|---|---|
| 4,339,426 A | | 7/1982 | Meares et al. |
| 5,093,042 A | | 3/1992 | Counsell et al. |
| 5,415,867 A | | 5/1995 | Minchey et al. |
| 5,514,379 A | * | 5/1996 | Weissleder et al. ......... 424/426 |
| 5,660,814 A | * | 8/1997 | Uggeri et al. .............. 424/9.36 |
| 5,720,720 A | * | 2/1998 | Laske et al. ................ 604/500 |
| 5,882,626 A | | 3/1999 | Epstein et al. |
| 6,435,714 B1 | | 8/2002 | Bruder |
| 6,438,198 B1 | | 8/2002 | Kohler |
| 6,442,229 B1 | | 8/2002 | Koehler et al. |

FOREIGN PATENT DOCUMENTS

EP 0 882 454 A3 12/1998
WO WO 93/06868 4/1993

OTHER PUBLICATIONS

Laske et al. 1997; Tumor regression with regional distribution of the targeted toxin TF-CRM100 in patients with malignant brain tumors. Nature Medicine 3(12): 1362-1368.*
Kobayashi et al.Jul. 1, 2001; Dynamic micro-magnetic resonance imaging of liver micro-metastasis in mice with a novel liver macromolecular magnetic resonance contrast agent DAB-AM64-(1B4M-Gd)64. Cancer Research 61: 4966-4970.*
Kroll et al. 1996; Increasing volume of distribution to the brain with interstitial infusion: Dose, rather than convection, might be the most important factor. Neurosurgery 38(4): 746-752.*
Lonser et al. 1998; Direct convective delivery of macromolecules to the spinal cord. J. Neurosurgery 89: 616-622.*
Wisneski et al. 1985; Absence of myocardial biochemical toxicity with a non ioninc contrast agent iopamidol. American Heart Journal 110 (3): p609-617; only the abstract is being provided.*
Wosilait et al. 1981; Competition between serum albumin and soluble fraction of liver for binding of warfarin and other drugs. Res Commun. Chem Pathol Pharamcol. 32(1): 113-122; only the abstract is being provided.*
Bobo et al., *Proc. Natl. Acad. Sci. USA* 91:2076-2080, 1994.
Chen et al., *J. Neurosurg* 90:315-320, 1999.
Debinski, *Cancer Invest* 20(5-6):801-809, 2002 (Abstract).

(Continued)

*Primary Examiner*—Karen Cochrane Carlson
(74) *Attorney, Agent, or Firm*—Klarquist Sparkman, LLP

(57) ABSTRACT

A method for monitoring and controlling convection enhanced delivery of a therapeutic agent to a target tissue is disclosed. A tracer that is detectable, for example, by magnetic resonance imaging (MRI) and/or by X-ray computed tomography (CT) is co-infused with the therapeutic agent and used to monitor the distribution of the therapeutic agent as it moves through the target tissue. The images obtained during delivery are used to confirm delivery of the therapeutic agent to the target tissue and to avoid exposure of tissue outside of the targeted area to the therapeutic agent. In addition, the signal intensity of the images may be used to confirm that the therapeutic agent has been delivered to the target tissue at a desired concentration.

29 Claims, 14 Drawing Sheets

OTHER PUBLICATIONS

Guridi et al., *J. Neurosurg.* 93:364-366, 2000.
Hall, *Neurosurgery* 46(3):544-551, 2000 (Abstract).
Hamilton et al., *Experimental Neurology* 168:155-161, 2001.
Kobayashi et al., "Monoclonal antibody-dendrimer conjugates enable radiolabeling of antibody with markedly high specific activity with minimal loss of immunoreactivity," http://link.springer-ny.com/link/service/journals/00259/contents/00/00293/s002590000293ch002.htm, downloaded Jun. 22, 2001 (Abstract).
Laske et al., *J. Neurosurg* 80:520-526, 1994.
Laske et al., *J. Neurosurg* 87:586-594, 1997.
Laske et al., *Nature Medicine* 3(12):1362-1368, 1997.
Lieberman et al., *J. Neurosurg.* 82:1021-1029, 1995.
Lieberman et al., *J. Neurosurg.* 92:928-934, 1999.
Lonser et al., *J. Neurosurg.* 89:610-615, 1998.
Lonser et al., *J. Neurosurg.* 89:616-622, 1998.
Lonser et al., *J. Neurosurg.* 97(4):905-913, 2002 (Abstract).
Maki et al., *Gang To Kagaku Ryoho.* 13(4 Pt 2):1603-1610, 1986 (Abstract).
Morrison et al., *Am. J. Physiol.* 266 (*Regulatory Integrative Comp. Physiol. 35*):R292-R305, 1994.
Morrison et al., *Am. J. Physiol.* 277 (*Regulatory Integrative Comp. Physiol. 46*):R1218-R1229, 1999.
Nguyen et al., *J. Neurosurg.* 98(3):584-590, 2003 (Abstract).
Oldfield et al., *Curr. Top. Microbiol. Immunol.* 234:97-114, 1998.
Ratliff et al., *J. Neurosurg.* 95:1001-1011, 2001.
Wood et al., *J. Neurosurg* (*Spine 1*), 90:115-120, 1999.
"X-ray Transmission Imaging," http://cfi.lbl.gov/~budinger/medTechdocs/Xray.html, downloaded Sep. 20, 2002.
Zirzow et al., *Neurochemical Research* 24(2):301-305, 1999.
Caravan et al., "Gadolinium(III) Chelates as MRI Contrast Agents: Structure, Dynamics, and Applications," *Chem. Rev.*, pp. 2293-2352, 1999.
Eichman et al., "Imaging of gold dendrimer nanocomposites in cells," *Mat. Res. Soc. Symp. Proc.* 676:Y9.3.1-Y9.3.11, 2001.
Kobayashi et al., "3D-Micro-MR Angiography of Mice Using Macromolecular MR Contrast Agents With Polyamidoamine Dendrimer Core With Reference to Their Pharmacokinetic Properties," *Magnetic Resonance in Medicine* 45:454-460, 2001.
Kobayashi et al., "Dynamic Micro-Magnetic Resonance Imaging of Liver Micrometastasis in Mice with a Novel Liver Macromolecular Magnetic Resonance Contrast Agent DAB-Am64-$(1B4M-Gd)_{64}$," *Cancer Research* 61:4966-4970, 2001.
Kobayashi et al., "Novel Intravascular Macromolecular MRI Contrast Agent With Generation-4 Polyamidoamine Dendrimer Core: Accelerated Renal Excretion With Coinjection of Lysine," *Magnetic Resonance in Medicine* 46:457-464, 2001.
Kobayashi et al., "Novel Liver Macromolecular MR Contrast Agent With a Polypropylenimine Diaminobutyl Dendrimer Core: Comparison to the Vascular MR Contrast Agent With the Polyamidoamine Dendrimer Core," *Magentic Resonance in Medicine* 46:795-802, 2001.
Kobyashi et al., "Renal tubular damage detected by dynamic micro-MRI with a dendrimer-based magnetic resonance contrast agent," *Kidney International* 61(6):1980-1985, 2002.
Konda, et al., "Specific targeting of folate-dendrimer MRI contrast agents to the high affinity folate receptor expressed in ovarian tumor xenografts," *MAGMA* 12:104-113. 2001.
Lam et al., "Analysis of In Vivo Imaging and Distribution of Macromolecules in CT and MRI via Convection Enhanced Delivery," *presented in a non-public forum to employees of the National Institutes of Health*, Summer 1998.
Malik et al., "Dendrimer-platinate: a novel approach to cancer chemotherapy," *Anti-Cancer Drugs* 10:767-776, 1999.
Sato et al., "Pharmacokinetics and Enhancement Patterns of Macromolecular MR Contrast Agent With Various Sizes of Polyamidoamine Dendrimer Cores," *Magnetic Resonance in Medicine* 46:1169-1173, 2001.
Tajarobi et al., "Transport of poly amidoamine dendrimers across Madin-Darby canine kidney cells," *International Journal of Pharmaceutics* 215:263-267, 2001.
"Monitoring Infusion of Protein into Brain by Computed Tomography," *NIH Bioengineering Symposium*, Feb. 1998.

\* cited by examiner

METHOD FOR CONVECTION ENHANCED DELIVERY OF THERAPEUTIC AGENTS

PRIORITY CLAIM

This is a § 371 U.S. National Stage of International Application No. PCT/US2003/030155, filed Sep. 24, 2003, which was published in English under PCT Article 21(2), which in turn claims the benefit of U.S. Provisional Application No. 60/413,673, filed Sep. 24, 2002. Both applications are incorporated herein in their entirety.

FIELD

The invention generally relates to convection enhanced delivery (CED) of therapeutic agents. More specifically, the invention relates to a method of monitoring the distribution of therapeutic agents as they move through solid tissue during CED.

BACKGROUND

Intrinsic diseases of the central nervous system (CNS), including the brain, the brainstem, the spinal cord and peripheral nerves, often result in serious morbidity, death or impairment of mobility because there is no effective surgical or medical therapy. Although an expanding number of potentially therapeutic compounds exist for treating these disorders, inadequate delivery of these agents to the CNS limits their effective use. Currently available delivery techniques rely on systemic or intrathecal drug administration, both of which have a number of inherent limitations. For example, systemic toxicity and the inability of many compounds to cross from the circulatory system to the CNS frequently restrict systemic delivery, and even if systemically delivered agents do enter the CNS, their distribution is either heterogeneous or non-targeted [see, for example, Langer, "New methods of drug delivery," *Science*, 249: 1527-1533 (1990); Morrison, "Distribution models of drug kinetics," in *Principles of Clinical Pharmacology*, Atkinson et al (eds), Academic Press, New York, pp 93-112 (2001); and Pardridge, "Drug delivery to the brain." *J Cereb Blood Flow Metab*, 17:713-731 (1997)]. Penetration into the nervous system following intrathecal delivery (including intrathecal injection, direct intratumoral injection, intracavitary instillation, or controlled release from polymer implants), like systemic delivery, relies on diffusion and also produces non-targeted, heterogeneous dispersion throughout the CNS [see, for example, Blasberg et al., "Intrathecal chemotherapy: brain tissue profiles after ventriculocisternal perfusion," *J Pharmacol Exp Ther*, 195:73-83 (1975)]. Potentially therapeutic substances have yet to be effective in the treatment of intrinsic diseases of the CNS due to the limitations of these delivery methods.

Convection-enhanced delivery (CED) may be used to overcome some of the restrictions associated with other delivery systems. CED utilizes a pressure gradient to infuse substances directly into the interstitial space of a solid tissue (interstitial infusion). Since CED relies on bulk (convective) flow, rather than diffusion, it can be used to distribute both small and large molecular weight substances over clinically relevant volumes within solid tissue [see, for example, Morrison et al., "Focal delivery during direct infusion to brain: role of flow rate, catheter diameter, and tissue mechanics," *Am J Physiol*, 277: R1218-1229 (1999) and Morrison et al., "High-flow microinfision: tissue penetration and pharmacodynamics," *Am J Physiol*, 266: R292-305 (1994)]. Furthermore, substances are delivered at relatively constant concentration throughout the volume of distribution.

Factors that influence delivery of a therapeutic agent by CED include the type of tissue infused (for example, white or gray matter) and the tissue binding properties, metabolism and microvascular permeability of the agent. In addition, the volumetric flow rate, duration of infusion, and the size of the cannula (or catheter) used to deliver an infusate may affect the distribution of therapeutic agents delivered by CED.

Of particular concern during CED is retrograde flow (backflow) along the shaft of the cannula that is used to deliver the infusate to a tissue. Backflow may cause infused therapeutic agents to reach unintended tissue, and cause underexposure of the intended target. Theoretical studies of the factors affecting backflow indicate that it may be minimized by using a small diameter cannula, and that minimal backflow may be maintained by offsetting an increase in flow rate with a similar decrease in cannula radius. However, control of backflow remains a concern, particularly if CED is used in a clinical setting.

Furthermore, while a number of studies of CED have shown that there is a roughly linear relationship between the volume of infusate delivered (volume of infusion) and the volume over which the infusate is ultimately distributed (volume of distribution), they also show that other factors that influence the spread of an agent delivered by CED may not always be known for a given subject. These factors include existence of preferential pathways for fluid flow in the target region (for example, fiber tracts in white matter) which may lead to asymmetrical agent distribution, variable cell receptor density that may affect the timing and extent of an agent's spread, and large target volumes that may require long infusion times or multiple sites of delivery.

Single photon emission computed tomography (SPECT) has been applied to visualize the spread of an agent delivered by CED, but the method does not offer sufficient resolution to provide details of agent distribution [see, for example, Laske et al., "Chronic interstitial infusion of protein to primate brain: determination of drug distribution and clearance with single-photon emission computerized tomography imaging," *J. Neurosurgery*, 87: 586-594 (1997)]. As such, SPECT provides only an estimate of the volume of distribution and no detailed information about the shape of the infusion envelope in the tissue.

Since many therapeutic agents, especially those used to destroy tissue, such as cancer tissue, are highly toxic, control over the site of delivery during CED is especially important in the clinical setting, where minimization of side effects is a concern. A method that enables more precise control over the CED process would help ensure proper delivery of therapeutic agents to target regions of tissue without exposure of surrounding tissue to the agents. Such a method would fill a long-felt and heretofore unmet need in the art.

SUMMARY OF THE DISCLOSURE

Methods are disclosed for delivering a therapeutic agent and accurately and rapidly imaging the distribution and/or the concentration of the therapeutic agent as it moves through a solid tissue during convection-enhanced delivery (CED). The methods are demonstrated to provide controlled and targeted delivery of therapeutic agents to substantially only to the intended targeted region of tissue, thereby, for example, increasing the safety with which highly toxic therapeutic agents may be delivered to sensitive tissues such as the brain. In one embodiment, a tracer, which is detectable by magnetic resonance imaging and/or X-ray computed tomography, is co-infused with a therapeutic agent and used to monitor the distribution and/or concentration of the therapeutic agent as it moves through the solid tissue. The movement of the tracer may be monitored to detect unwanted delivery of the therapeutic agent outside of a target volume within a solid tissue, and to verify that the therapeutic agent is reaching the target at the proper concentration. In some embodiments, the tracer is conjugated directly to the therapeutic agent. Alternatively, a separate tracer that spreads through the tissue at a rate that may be accurately correlated to the spread of the therapeutic agent functions as a surrogate for following the spread of the therapeutic agent. In either instance, the speed with which images may be generated, coupled with an unexpectedly accurate correlation between the tracer distribution and the therapeutic agent's distribution, make it possible to deliver therapeutic agents substantially only to the targeted region of tissue, for example, substantially only to the region of a tissue occupied by a tumor. Furthermore, an accurate correlation between imaging signal intensity and concentration of the therapeutic agent is also demonstrated, making it possible to confirm delivery of a therapeutic agent to a targeted region of a tissue in a desired concentration.

DETAILED DESCRIPTION

Figure 1:
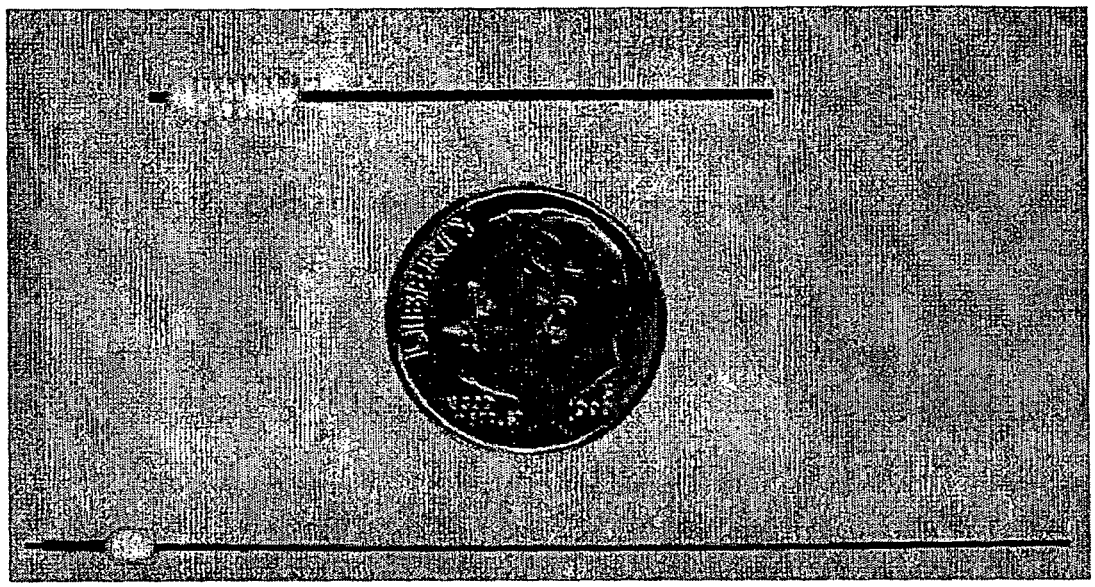
FIG. 1 is a photograph showing a cannula system for CED. The outer cannula (below dime) and the inner infusion cannula (above dime) are shown separately.

The discussion and examples that follow are best understood with reference to the following abbreviations and terms.

I. Abbreviations

CED—convection enhanced delivery

MRI—magnetic resonance imaging

CT—X-ray computed tomography

1B4M—2-(p-isothiocyanotobenzyl)-6-methyldiethylen-etriamine pentaacetic acid.

QAR—quantitative autoradiography

HSA-(Gd-1B4M)$_5$—human serum albumin conjugated to 5 gadolinium chelates of 2-(p-isothiocyanotobenzyl)-6-methyldiethylenetriamine pentaacetic acid.

BSA-(Gd-1B4M)$_5$—bovine serum albumin conjugated to 5 gadolinium chelates of 2-(p-isothiocyanotobenzyl)-6-methyldiethylenetriamine pentaacetic acid.

DAB-Am-64-(1B4M-Gd)$_{64}$—polypropylene tetrahexacontaamine dendrimer with a diaminobutane core conjugated to 64 1B4M-Gd chelates.

$V_i$—volume of infusion $V_d$—volume of distribution

GFAP—anti-glial fibrillary acidic protein antibody

II. Terms

Unless otherwise explained, all technical and scientific terms used herein have the same meaning as commonly understood by one of ordinary skill in the art to which this invention belongs. The singular terms "a," "an," and "the" include plural referents unless the context clearly indicates otherwise. Similarly, the word "or" is intended to include "and" unless the context clearly indicates otherwise.

"Comprising A or B" means including A or B or including A and B unless otherwise indicated.

The term "subject" refers to animals, including mammals. Examples of subjects include humans and veterinary animals such as dogs, cats, cattle, sheep, horses etc.

The term "imaging" refers to any technique for forming a representation of anatomical structures within a body. Examples of imaging techniques include sonic techniques (such as ultrasound) and electromagnetic techniques, for example, radiological approaches using X-rays (such as CT or conventional X-ray), or a magnetic field in combination with radio waves (for example, MRI).

The term "solution" refers to a composition comprising a solvent and a solute, and includes true solutions and suspensions. Examples of solutions include a solid, liquid or gas dissolved in a liquid and particulates or micelles suspended in a liquid.

As used herein, the term "convective insterstitial infusion" refers to convection enhanced delivery. Convective interstial ifusion is a method of high-flow microinfusion which provides convection-enhanced delivery of therapeutic agents. The method involves positioning the tip of an infusion catheter within a tissue structure and supplying a solution comprising a therapeutic agent through the catheter while maintaining a pressure gradient from the tip of the catheter during infusion. After the infusion catheter is positioned in a tissue situs, it is connected to a pump which delivers a solution and maintains a desired pressure gradient throughout delivery of the agent. Convection enhanced delivery is described, for example, in U.S. Pat. No. 5,720,720, which is incorporated by reference herein. The term "infusate" refers to a solution delivered by convective interstitial infusion.

As used herein, "therapeutic agent" refers to any molecule that may be delivered to a solid tissue to treat a condition of the tissue. Therapeutic agents include antineoplastic agents, radioiodinated compounds, toxins (including protein toxins), cytostatic or cytolytic drugs, genetic and viral vectors, neurotrophic factors, cytokines, enzymes and agents for targeted lesioning of specific sites. Therapeutic agents also include any therapeutic molecule which is targeted selectively to a cell expressing a particular antigen, for example, immunotoxins (see, for example, Laske et al., "Tumor regression with regional distribution of the targeted toxin TF-CRM107 in patients with malignant brain tumors," *Nature Medicine,* 3: 1362-1368, 1997).

The term "tracer" refers to a substance that is detectable by imaging techniques, such as magnetic resonance- or X-ray-based imaging, for example, MRI or CT (In some examples, a tracer is a molecule that contains at least one imaging moiety). In particular examples, the tracer is or is not a therapeutic agent itself. In others, the tracer is conjugated to a therapeutic agent. A tracer and a therapeutic agent, although separate, also may be delivered together by convective interstitial infusion and the tracer monitored to follow the process of infusion. The term "surrogate tracer," where used, refers to a molecule other than a therapeutic agent and not conjugated thereto that is detectable by imaging, for example, by MRI or CT.

An "imaging moiety" refers to a group of atoms detectable in an imaging technique, for example, in a magnetic resonance- or X-ray-based technique, such as MRI or CT. "MR contrast moiety" refers to a group of atoms detectable in an MRI experiment by virtue of differential contrast to surrounding tissues or structures. "X-ray contrast moiety" refers to an imaging moiety that is detectable by an X-ray imaging technique (such as CT) by virtue of differential contrast to surrounding tissues or structures. Of course, some imaging moieties may be both an MR contrast moiety and an "X-ray contrast moiety."

The term "target tissue" refers to a physical (usually anatomical) target, for example, in the brain. Examples of such target tissues include a tumor, such as a brain tumor, a cyst, a seizure focus in the brain to be ablated, or a particular neuroanatomic substructure (such as the pons, midbrain, thalamus, optic tract or occipital cortex). The target tissue may be an entire physical target or some portion thereof to which delivery of a therapeutic agent is desired.

The phrase "substantially only to the target tissue" refers to delivery of a therapeutic agent to a target tissue without significant delivery of the agent outside of the target tissue, which is characterized by a steep drop in concentration of the therapeutic agent (as reflected, for example, by a steep drop in a signal due to a tracer used to follow the distribution of the therapeutic agent) at the periphery of the target tissue. For example, delivery substantially only to the target tissue may be reflected by a drop in therapeutic agent concentration (or tracer signal intensity) of more than 75% (such as more than 85% or 95%) over a distance of a few millimeters (such as a distance of 1-4 mm) from the periphery of the target tissue.

The act of "monitoring" refers to obtaining serial images of the tracer as it spreads (along with or in proportion to the spread of the therapeutic agent) within a solid tissue. By monitoring the spread of the tracer, the location and volume of distribution of the infusate within the tissue may be determined at any time during the infusion process. Serial images may be obtained at any rate up to the maximum rate that the MRI or CT instrument can obtain images. For example, serial images may be obtained at intervals ranging from a few milliseconds to hours, but more typically at intervals of minutes, such as intervals of 1, 2, 5, 10, 15, 20 or 30 minutes. The interval between serial images may be varied during infusion. In some instances, it may be desirable to obtain images at short intervals (for example, every 5, 10, or 15 seconds) at the beginning of the infusion process to detect backflow along the cannula, or to verify that the infusate is entering the desired target tissue. Once delivery to the proper site is confirmed, the interval between images may be lengthened, and the images used to follow the progress of infusion, for example, to determine if infusate is reaching tissue outside of the targeted area or if the desired volume of distribution has been reached. Where multiple infusions are needed to complete treatment of a particular region of solid tissue, the volume of distribution of the first infusion (and subsequent infusions prior to the last one) may be used to guide placement of the cannula so that the untreated portions of the region of solid tissue may be effectively treated by a subsequent infusion.

The phrase "a predetermined volume of distribution" refers to a region of a solid tissue into which delivery of a therapeutic agent is desired. For example, the predetermined volume may correspond with the volume occupied by a tumor, or the predetermined volume may be a particular region of the brain that is targeted for destruction (e.g. the medial globus pallidus). The predetermined volume of distribution may be "substantially similar" to the volume of distribution observed for a tracer that is being monitored to follow the infusion. "Substantially similar" refers to a difference in volume or mobility of less than 20%, such as less than 10% or less than 5%, between the volumes of distribution or mobilities of the tracer and the therapeutic agent. The predetermined volume of distribution also may be smaller or greater than the tracer's observed volume of distribution, in which case, a correlation between the volume of distribution of the tracer and the volume of distribution of the therapeutic agent may be used to convert the observed tracer distribution to a therapeutic agent distribution. Thus, by monitoring the distribution of the tracer, infusion may be ceased when the predetermined volume of distribution is reached, regardless of the relative mobilities of the tracer and therapeutic agent in the tissue. A determination of whether or not the tracer has a mobility that is substantially similar to a therapeutic agent, or a determination of how the volume of distribution of a tracer correlates to the volume of distribution of the therapeutic agent may, for example, be determined by animal studies which compare the volume of distribution of a radiolabeled therapeutic agent (determined, for example, by QAR) to the volume of distribution determined by MRI or CT for a co-infused tracer (see, Examples 1 and 2).

The term "protein" refers to proteins, polypeptides and fragments thereof. Examples of proteins include albumins, such as human or bovine serum albumin; immunoglogulins such as IgG; metalloproteins such as ferritin, hemoglobin, and myoglobin; glycoproteins; lipoproteins; transferring; viral coat proteins; and enzymes such as acetyltransferases.

The disclosed materials, methods, and examples are illustrative only and not intended to be limiting. Various embodiments are illustrated by the following non-limiting Examples.

III. EXAMPLES

In one aspect, a method is disclosed for convection enhanced delivery of a therapeutic agent by providing a solution comprising the therapeutic agent and a tracer, delivering the solution to a solid tissue by convective interstitial infusion, monitoring the distribution of the tracer as it moves through the solid tissue, and ceasing delivery of the solution to the solid tissue when the therapeutic agent is distributed in a predetermined volume within the solid tissue. The movement of the tracer through the solid tissue may be monitored by an imaging technique such as magnetic resonance imaging (such as MRI) or X-ray, for example, computed tomography (CT). If the tracer may be assumed to, or is known to have a mobility in the solid tissue that is substantially similar to the therapeutic agent, delivery may be ceased when the tracer is observed to reach a predetermined volume or region of distribution, or reach or exceed the borders of the target tissue. Delivery may also be ceased before the borders of the target tissue are reached by the tracer if it is expected or known that that the therapeutic agent has a greater mobility in the tissue than the tracer. For example, where a correlation has been established between the mobilities of the tracer and the therapeutic agent, delivery may be ceased when the observed distribution of the tracer corresponds to a desired distribution of the therapeutic agent.

If the tracer does not have a mobility that is substantially similar to the therapeutic agent, or cannot be assumed to have a substantially similar mobility as the therapeutic agent (for example, because the agent is highly toxic and delivery of the agent will damage sensitive tissues such as brain tissue outside of the target tissue) the volume of distribution of the tracer that is observed may be converted to a volume of distribution of the therapeutic agent using a previously established correlation between the two. Thus, monitoring the volume of distribution for the tracer may be used to determine if the therapeutic agent has reached the predetermined volume of distribution, and, for example, has been delivered substantially only to the target tissue.

In some embodiments, the tracer may comprise a metal chelate. In one embodiment, the tracer comprises a metal chelate conjugated to the therapeutic agent, and, in others, the tracer comprises a metal chelate conjugated to a carrier molecule. Although conjugation typically refers to formation of a covalent bond between the metal chelate and either the therapeutic agent or the carrier molecule, other types of bonds (for example, ionic, dipole-dipole, or van der Waals) may suffice in some embodiments.

A metal chelate is a complex of a metal ion and a metal chelating group (a group of atoms that serves to bind the metal ion). Examples of metal chelating groups include natural and synthetic amines, porphyrins, aminocarboxylic acids, iminocarboxylic acids, ethers, thiols, phenols, glycols and alcohols, polyamines, polyaminocarboxylic acids, polyiminocarboxylic acids, aminopolycarboxylic acids, iminopolycarboxylic acids, nitrilocarboxylic acids, dinitrilopolycarboxlic acids, polynitrilopolycarboxylic acids, ethylenediaminetetracetates, diethylenetriaminepenta or tetraacetates, polyethers, polythiols, cryptands, polyetherphenolates, polyetherthiols, ethers of thioglycols or alcohols, polyaminephenols, all either acyclic, macrocyclic, cyclic, macrobicyclic or polycyclic, or other similar ligands which produce stable metal chelates or cryprates (including sepulchrates, sacrophagines, and crown ethers).

Specific examples of metal chelating groups include 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N(2-aminoethyl)amide and DOTA-N-(2-aminophenethyl)amide, BOPTA, HP-DO3A, DO3MA, DTPA, and various derivatives thereof. Additional examples are provided in Caravan et al., Chem. Rev., 99: 2293-2352 (1999) and in U.S. Pat. Nos. 5,246,692, 5,292,868 and 5,434,287. A particularly disclosed example of a metal chelating group is 2-(p-isothiocyanotobenzyl)-6-methyldiethylenetriamine pentaacetic acid (1B4M). Since it is advantageous for in vivo imaging to select a metal chelating group capable of tightly binding a metal ion, a high stability constant for the metal chelate is desired.

Metals ions of the metal chelates may be paramagnetic ions if the imaging agent is to be used as a MRI contrast agent. Suitable metal ions include those having atomic numbers of 22-29 (inclusive), 42, 44 and 58-70 (inclusive) and have oxidation states of +2 or +3. Examples of such metal ions are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III).

If the macromolecular imaging agent is to be used as an X-ray contrast agent, the metal ion may be selected from the ions of W, Bi, Hg, Os, Pb, Zr, lanthanides, and combinations thereof. If a combined MRI/X-ray contrast agent is desired, the metal ion may be selected from the paramagnetic lanthanide ions. If a radiographic imaging agent is desired, the metal may be radioactive, such as the radioactive isotopes of In, Tc, Y, Re, Pb, Cu, Ga, Sm, Fe, or Co.

Bifunctional chelating agents may be used to form conjugates of a metal chelate and either a therapeutic agent or a carrier molecule. A bifunctional chelating agent is a molecule capable of forming a bond with another molecule, such as a protein or a dendrimer, and also capable of forming a metal chelate by binding a metal ion. Appropriate bifunctional chelating agents therefore include a reactive group and a metal chelating group, such as those described previously.

The reactive group of a bifunctional chelating agent is a group of atoms that that will undergo a reaction with another molecule to form a bond, such as a covalent bond. Examples of reactive groups include carboxylic acid groups, diazotiazable amine groups, N-hydroxysuccinimidyl, esters, aldehydes, ketones, anhydrides, mixed anhydrides, acyl halides, maleimides, hydrazines, benzimidates, nitrenes, isothiocyanates, azides, sulfonamides, bromoacetamides, iodocetamides, carbodiimides, sulfonylchlorides, hydroxides, thioglycols, or any reactive group known in the art as useful for forming conjugates. If, for example, the therapeutic agent or carrier molecule is a protein or a dendrimer having surface amine groups, the reactive group may be any functional group capable of undergoing reaction with an amine group.

Specific examples of bifunctional chelating agents include bifunctional diethylenetriaminepentaacetic acid (DTPA) derivatives such as those disclosed in U.S. Pat. No. 5,434,287 to Gansow et al. Other examples include polysubstituted diethylenetriaminepentaacetic acid chelates such as those described by Gansow et al. in U.S. Pat. No. 5,246,692. Bifunctional chelating agents comprising 1,4,7,10-Tetraazacyclododecane-N,N',N'',N'''-tetraacetic acid (DOTA) and its derivatives are also useful. Examples of bifunctional DOTA derivatives are provided in U.S. Pat. No. 5,428,154 to Gansow et al. and references therein.

Tracers may be prepared by reacting a therapeutic molecule or a carrier molecule with the reactive group of a bifunctional chelating agent and then reacting the metal chelating group of the bifunctional chelating agent with a metal ion. Alternatively, a metal ion is reacted with the metal chelating group of the bifunctional chelating agent prior to reacting the reactive group of the bifunctional chelating agent with a surface groups of the dendrimer. Metal chelation is typically carried out in a solution, and desirably avoids the use of strong acids or bases.

Methods for reacting bifunctional chelating agents with other molecules (such as proteins, therapeutic agents and dendrimers) to form conjugates, and for forming metal chelates thereof, are well known. For example, methods for forming metal chelate conjugates of proteins are disclosed in U.S. Pat. Nos. 5,246,692, 5,292,868, 5,364,613, 5,434,287 and 6,274,713, and in European Patent EP0882454. Methods for forming metal chelate conjugates of dendrimers are disclosed, for example, in U.S. Pat. No. 5,834,020 and in PCT Publication WO 93/06868.

In other embodiments, where X-ray imaging (such as CT) is used to monitor CED, the tracer may comprise a radiopaque material. Radiopaque materials also may be used to label proteins (such as albumins) and dendrimers (such as DAB dendrimers). Suitable radiopaque materials are well known and include iodine compounds, barium compounds, gallium compounds, thallium compounds, and the like. Specific examples of radiopaque materials include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosumetic acid, iotasul, iotetric acid, iothalamic acid, iotroxic acid, ioxaglic acid, ioxotriroic acid, ipodate, meglumine, metrizamide, metrizoate, propyliodone, and thallous chloride.

Where the tracer comprises a carrier molecule, the carrier molecule may be any molecule other than the therapeutic agent. In some embodiments, the carrier molecule is selected so the tracer will have a mobility (or other property related to movement and clearance from the tissue) in a solid tissue that is comparable to the therapeutic agent.

Examples of suitable carrier molecules include proteins and dendrimers. Particular examples of proteins include albumins such as human serum albumin and bovine serum albumin.

Dendrimers are highly branched, often spherical molecules synthesized by reiterative reaction sequences starting from a core molecule having multiple reactive groups. Particular types of dendrimers include polyalkyelenimine dendrimers and polyamidoamine dendrimers. Particular examples and methods of producing polyamidoamine dendrimers, amongst other types, are provided in U.S. Pat. Nos. 4,507,466, 4,558,120, 4,568,737, 4,694,064, 4,737,550 and 4,837,599. Polyamidoamine (PAMAM) dendrimers are available commercially, for example, from Aldrich (Milwaukee, Wis.). Examples of polyalkylenimine dendrimers include polypropylenimine, polybutylenimine, or other dendrimers having C3 or higher alkyl chain branches, such as C3-C10 alkyl chain branches, extending out from a core molecule. Examples of suitable core molecules include ammonia, ethylenediamine, propylenediamine, diaminobutane and other polyamines such as tris-aminoethylamine, cyclene, hexaazacyclooctadecane, 1,5 diaminopentane, tethylenetriamine, triethylenetetramine, 1,4,8,11-tetraazaundecane, 1,5,8,12-tetraazaundodecane, and 1,5,9,13-tetraazatridecane.

One particular example of a polypropylenimine dendrimer is a polypropylenimine dendrimer with a diaminobutane core (DAB dendrimer). Examples of polypropylenimine dendrimers also include those with core molecules such as ammonia, ethylenediamine, propylenediamine, or some other polyamine. Typically, the surface of the polypropylenimine dendrimer will have one or more amino groups. However, some or all of the surface amino groups maybe modified, for example, to provide other reactive groups or charged, hydrophilic, and/or hydrophobic groups on the surface.

A particular example of a DAB dendrimer is polypropylenimine tetraamine dendrimer, Generation 1 [DAB-Am-4; N,N,N',N'-tetrakis(3-aminopropyl)-1,4-butanediaminepolypropylenimine tetramine]. DAB-Am4 denotes a diaminobutane-core polypropylenimnine dendrimer having 4 amino groups at its surface. Additional examples include polypropylenimine octaamine dendrimer, Generation 2.0 [DAB-Am-8; 4,17-bis(3-aminopropyl)-8,13-bis[3-[bis(3-aminopropyl)-amino]propyl]-4,8,13,17-tetraazaeicosane-1, 20-diamine], having 8 amino groups on its surface; polypropylenimine hexadecaamine dendrimer, Generation 3.0 [DAB-Am-16; [—CH$_2$CH$_2$N(CH$_2$)$_3$N[(CH$_2$)$_3$NH$_2$]$_2$]$_2$]$_2$], having 16 amino groups on its surface; polypropylenimine dotriacontaamine dendrimer, Generation 4.0 [DAB-Am-32; [—CH$_2$CH$_2$N(CH$_2$)$_3$N[(CH$_2$)$_3$NH$_2$]$_2$]$_2$]$_2$]$_2$], having 32 amino groups on its surface; polypropylene tetrahexacontaamine dendrimer, Generation 5.0 [DAB-Am-64; [—CH$_2$CH$_2$N(CH$_2$)$_3$N[(CH$_2$)$_3$NH$_2$]$_2$]$_2$]$_2$]$_2$]$_2$], having 64 amino groups on its surface; and higher generation DAB-Am dendrimers such as DAB-Am-128, DAB-Am-256, and DAB-Am-512.

DAB-Am dendrimers of generations 1.0, 2.0, 3.0, 4.0 and 5.0 are commercially available from Aldrich (Milwaukee, Wis.). DAB-Am dendrimers also may be synthesized from a diaminobutane initiator core according to the methods disclosed in Womer, and Mulhaupt, *Angew Chem., Int. Ed. Engl*, 32: 1306-1308, 1993. Similar methods are also described by de Brabander-van den Berg and Meijer (*Angew Chem., Int. Ed. Engl*, 32: 1308, 1993). Polypropylenimine dendrimers having other initiator cores, such as ammonia, ethylenediamine, propylenediamine, and other polyamines may be synthesized according to these methods. Similar schemes may be used to synthesize polybutylenimine and higher polyalkylenimine dendrimers.

Therapeutic agents include antineoplastic agents, radio-iodinated compounds, toxins (including protein toxins), cytostatic or cytolytic drugs, neurotrophic factors, cytokines, enzymes and agents for targeted lesioning of specific sites. Therapeutic agents also include any therapeutic molecule which is targeted selectively to a cell expressing a particular antigen, for example, an immunotoxin (see, for example, Laske et al., "Tumor regression with regional distribution of the taargeted toxin TF-CRM107 in patients with malignant brain tumors," *Nature Medicine*, 3: 1362-1368, 1997). Examples of antineoplastic therapeutics include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-alpha, lomustine, mercaptopurne, methotrexate, mitotane, procarbazine HCl, thiognanine, vinblastine sulfate and vincristine sulfate.

Immunotoxins combine the toxicity of natural plant and bacterial proteins with the tissue-specific binding capacity of antibodies, more particularly monoclonal antibodies. For example, toxins such as pokeweed anti-viral protein, cholera toxin, pertussis toxin, ricin, gelonin, abrin, diphtheria exotoxin, or Pseudomonas exotoxin may be conjugated to an antibody. Toxin moieties can also be high energy-emitting radionuclides such as cobalt-60.

Numerous techniques suitable for binding various molecules (including toxin and MR or CT imaging moieties) to antibodies have been established. Iodination, for example, may be accomplished using the chloramine-T method described by S. Mills, et al., [123]I-Radiolabeling of Monoclonal Antibodies for In Vivo Procedures, Hybridoma 5: 265-275 (1986). This technique may be used to effect iodination to render the antibody radiopaque, or to attach a radionuclide, such as $^{125}$I or [131]I. A number of techniques exist for attaching various molecules, such as small molecules, enzymes and proteins, to antibodies. For example, many carboxylic acid-containing compounds (such as methotrexate) can be conjugated to immunoglobulins through an active ester intermediate, formed, for example, by reacting the compound with N-hydroxysuccinimide and dicyclohexylcarbodiimide (see, for example, Deguchi, et al., "Effect of Methotrexate-Monoclonal Anti-Prostatic Acid Phosphatase Antibody Conjugate on Human Prostate Tumor," *Cancer Res*. 46: 3751-3755 (1986)). Other therapeutic agents, such as chlorambucil, will bind directly to the antibodies at low pH (see, for example, Ghose, et al., "Immunochemotherapy of Human Malignant Melanoma with Chloroambucil-Carrying Antibody," *Europ. J. Cancer* 11: 321-326 (1975)). Amino sugar-containing drugs such as adriamycin and daunomycin may be covalently bound to antibodies by periodate oxidation of the drug, followed by linking of the oxidized drug to the immunoglobulin and subsequent reduction of the product with sodium borohydride [see, for example, Hurwitz, et al., "The Covalent Binding of Daunomycin and Adriamycin to Antibodies," *Cancer Res*. 35: 1175-1181 (1975)].

Conventional techniques also exist for binding other proteins to antibodies. For example, free thiol groups may be introduced into the antibody by reacting antibody with N-succininiidyl-3-(2-pyridyldithio)propionate (SPDP) to introduce 2-pyridyl disulphide groups, which may then be reduced with dithiotreitol to leave free thiol groups. The protein to be bound to the antibody is then incubated with SPDP. Upon mixing the SPDP-modified protein with the antibody containing free thiol groups, the two materials become bound.

Other known techniques, such as the use of dextran T-10 spacers to increase the number of drug moieties linked to antibody molecules can be employed, as can mixed anhydride methods of drug conjugation. The compound 1-ethyl-3-(3-dimethylaminopropyl) carbodiimide hydrochloride (ECDI) may be used to bind amino-containing drugs to the carboxyl groups of antibodies. Alternatively, glutaraldehyde may be used for cross-linking between free amino groups of the antibody and amino groups in the compound to be conjugated thereto.

Radionuclides and imaging moieties may also be attached to antibodies by reacting the bifunctional chelating agents discussed above with an antibody. Still other suitable techniques include the iodogen method disclosed in M. Pimm, et al., "In Vivo Localization of Anti-Osteogenic Sarcoma 791T Monoclonal Antibody," *Int. J. Cancer* 30: 75 (1982), and direct iodination with radioactive sodium iodide.

Regardless of whether the tracer is comprised of the therapeutic agent or a carrier molecule, the tracer is delivered in an amount sufficient to produce detectable differences in the image intensity of the solid tissue using either or both of MRI or CT. For MRI, such differences may be detected in either a $T_1$- or $T_2$-weighted image taken at some time after the imaging agent is administered. The difference may be due to either an increase or a decrease in the intensity of the solid tissue relative to surrounding tissue when compared to an image of the solid tissue obtained before administration of the agent. In particular embodiments, a detectable difference in MRI image intensity may be provided by delivering between about 0.001 mmol Gd/kg and about 0.10 mmol Gd/kg, for example, delivering between about 0.003 mmol Gd/kg and about 0.03 mmol Gd/kg. Imaging may begin anywhere from about 1 min to about 2 hrs after administration, such as between about 3 minutes and 60 minutes after administration.

During CED, the solution delivered to the solid tissue may be delivered at a rate between 0.1 µL/min and 15 µL/min.

Example 1

This example describes the preparation and characterization of a tracer comprising a protein conjugated to a metal chelate, and its use in following, in real time and in vivo, CED in the primate brainstem using MRI.

2-(p-isothiocyanotobenzyl)-6-methyldiethylenetriamine pentaacetic acid (1B4M) [see, Brechbiel and Gansow, *Bioconjug Chem*, 2:187-194 (1991)] was conjugated to human serum albumin (HSA) by modification of a previously described method [see, Mirzadeh et al., "Radiometal labeling of immunoproteins: covalent linkage of 2-(4- isothiocyanatobenzyl)diethylenetriaminepentaacetic acid ligands to immunoglobulin," *Bioconjug Chem* 1:59-65 (1990)]. Briefly, 100 to 150 mg of HSA was dissolved in 20 ml of 50 mM sodium bicarbonate, 0.15 M NaCl at pH 8.5. To this solution, 45 mg 1B4M dissolved in 1 ml $H_2O$ (initial ratio of ligand to HSA of 30) was then added. The reaction mixture was rotated at room temperature overnight. The unreacted or free ligand was then separated from HSA conjugate by centrifugation. The final ligand to HSA ratio (CL/HSA) was then determined spectrophotometrically [see, Pippin et al, "Spectrophotometric method for the determination of a bifunctional DTPA ligand in DTPA-monoclonal antibody conjugates," *Bioconjug Chem* 3:342-334 (1992)]. The final volume of the purified HSA-1B4M was adjusted to deliver a concentration of approximately 10 mg/mL HSA.

Gd (III) was then reacted with the HSA-1B4M at an initial 2:1 molar ratio (Gd/1B4M) using a standard solution of Gd (III) $[Gd(NO_3)_2]$ at $6.42\times10^{-3}$ M. The pH of the Gd (III) solution was adjusted to 4.5 to 5.0 using 5 M $NH_4OAc$ and was added to HSA-1B4M dropwise while mixing the reaction. The mixture was allowed to proceed for 5 to 6 hrs at room temperature with rotation. The unreacted Gd (III) was removed by adding 0.5 ml of 0.1 M EDTA solution, followed by centrifugation. The final concentration of albumin was determined spectrophotometrically by measuring the absorbance at 280 nm. The percent of Gd (III) incorporation was determined by repeating the measurement of the number of chelating agents on the protein and noting the decrease due to their occupation by Gd (III). Each HSA molecule was linked to 5 Gd molecules. A stock solution of the Gd-albumin conjugate (28 mg/ml) in phosphate buffered saline was then infused into the animals. The formula of the conjugate is believed to be albumin-(Gd-1B4M)$_5$.

The relative lack of toxicity of the Gd-albumin conjugate was demonstrated in rats. All animal investigations were conducted in accordance with the National Institutes of Health guidelines on the use of animals in research, and were approved by the Animal Care and Use Committee of the National Institute of Neurological Disorders and Stroke. Adult male rats (Sprague-Dawley; n=12) weighing between 300 to 400 grams were anesthetized with isoflurane (2%) and placed in a Kopf stereotactic frame. A sagittal incision was made through the scalp to the level of the skull. A burr hole was placed over the right frontal region. A 32-gauge cannula attached to a 25 µl Hamilton syringe filled with Gd-bound albumin was stereotactically placed in the right striatum. The coordinates for placement of the cannula tip in the striatum were 0.5 mm anterior to bregma, 2.8 mm right of midline, and 5 mm below the level of the dura.

To distribute the infusate using convection, a non-compliant, gas-tight, infusion apparatus that has been described in detail previously was used (see, Lonser et al., "Direct convective delivery of macromolecules to the spinal cord," *J Neurosurg* 89:616-622 (1998)). Briefly, the apparatus consists of a Harvard syringe pump that generates a continuous pressure gradient that is transmitted through a hydraulic drive that is attached to the infusate syringe plunger. Using this system, 10 µL Gd-albumin was delivered at a rate of 0.5 µL/minute into the striatum.

After the completion of the infusion, the animals were allowed to awaken. They were observed daily for clinical deficits, and euthanized at the end of the observation period (3 to 60 days). Upon euthanization, the brains were immediately removed and frozen at −70° C. The brains were then cut coronally in 20 µm-thick serial sections on a cryostat at −18° to −20° C. Tissue sections were cut through the entire brain. Sections were stained with hematoxylin and eosin, Luxol fast blue and Nissl. Immunohistochemistry for glial fibrillary acidic protein was performed.

The MRI characteristics of the Gd-albumin conjugate were also demonstrated in primates. Again, all animal investigation was conducted in accordance with the National Institutes of Health guidelines on the use of animals in research, and was approved by the Animal Care and Use Committee of the National Institute of Neurological Disorders and Stroke. Three adult Rhesus primates (*Macaca mulatta*) underwent CED of the Gd-albumin conjugate to the pontine region of the brainstem. After anesthesia had been induced in the animals, they were intubated, and given halothane general endotracheal anesthesia. The animal's temperature, heart rate, oxygen saturation, electrocardiographic responses, and end-tidal $PCO_2$ were monitored. The head of the animal was then secured into a Kopf stereotactic frame. Using sterile technique, a midline skin incision was made from the anterior to the posterior aspect of the vertex of the animal skull. Self-retaining retractors were placed within the wound to expose the underlying skull. A burr hole (1.0 cm) was placed over the stereotactically determined entry point, and underlying dura was then incised. The outer guide cannula (see, FIG. 1; outer diameter 0.027 in.; inner diameter 0.020 in.) was then stereotactically placed through the dural opening along the target trajectory to a level 1.5 cm above the desired pontine target. The outer guide cannula was then secured in place with methylmethacrylate. The inner cannula (see, FIG. 1; outer diameter 0.014 in.; inner diameter 0.006 in.), after being connected to the infusion apparatus, was then placed through the outer guide cannula to the target (see, FIG. 1). The animal was then placed in the MR-scanner for imaging studies during infusion.

Again, to distribute infusate into the brainstem using convection, a non-compliant delivery system that is gas-tight with no dead volume was used. A Harvard syringe pump was used to generate continuous pressure throughout the infusion. During infusion, the pressure was transmitted from the pump to a glass, gas-tight, infusate-filled Hamilton syringe (250 µL total volume) that was connected to polyetheretherketone (PEEK) tubing (outer diameter 0.23; inner diameter 0.050 in.). The PEEK tubing was attached directly to the inner infusion cannula that was placed directly into the pontine region of the brainstem. Infusions were performed at rates between 0.25 to 1.0 µl/minute.

Figure 3:
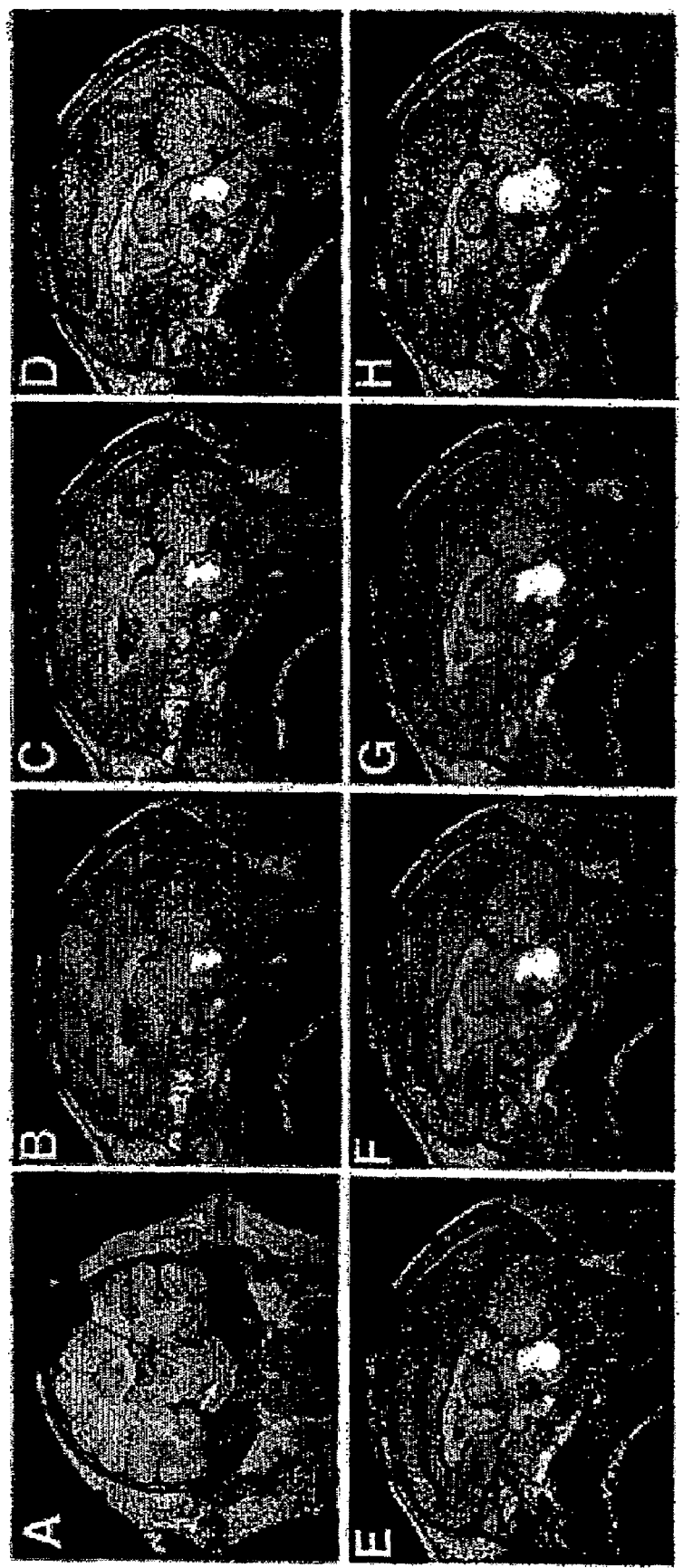
FIG. 3 is a series of real-time T1-weighted magnetic resonance images in the coronal (A) and mid-sagittal planes (B-H) at various time points during CED infusion of albumin-$(Gd-1B4M)_5$ into the pontine and midbrain regions of the brainstem (total volume of infusion 85 µl). The coronal image (A) demonstrates the position of the inner infusion cannula tip (arrow) just before starting the infusion of albumin-$(Gd-1B4M)_5$, and the mid-sagittal images (B-H) reveal that the region infused with albumin-$(Gd-1B4M)_5$ (white area) increased as the infusion progressed. The various total volumes of infusion shown here as examples include 7.5 µl (B), 15 µl (C), 30 µl (D), 40 µl (E), 50 µl (F), 65 µl (G), and 85 µl (H).
Figure 4:
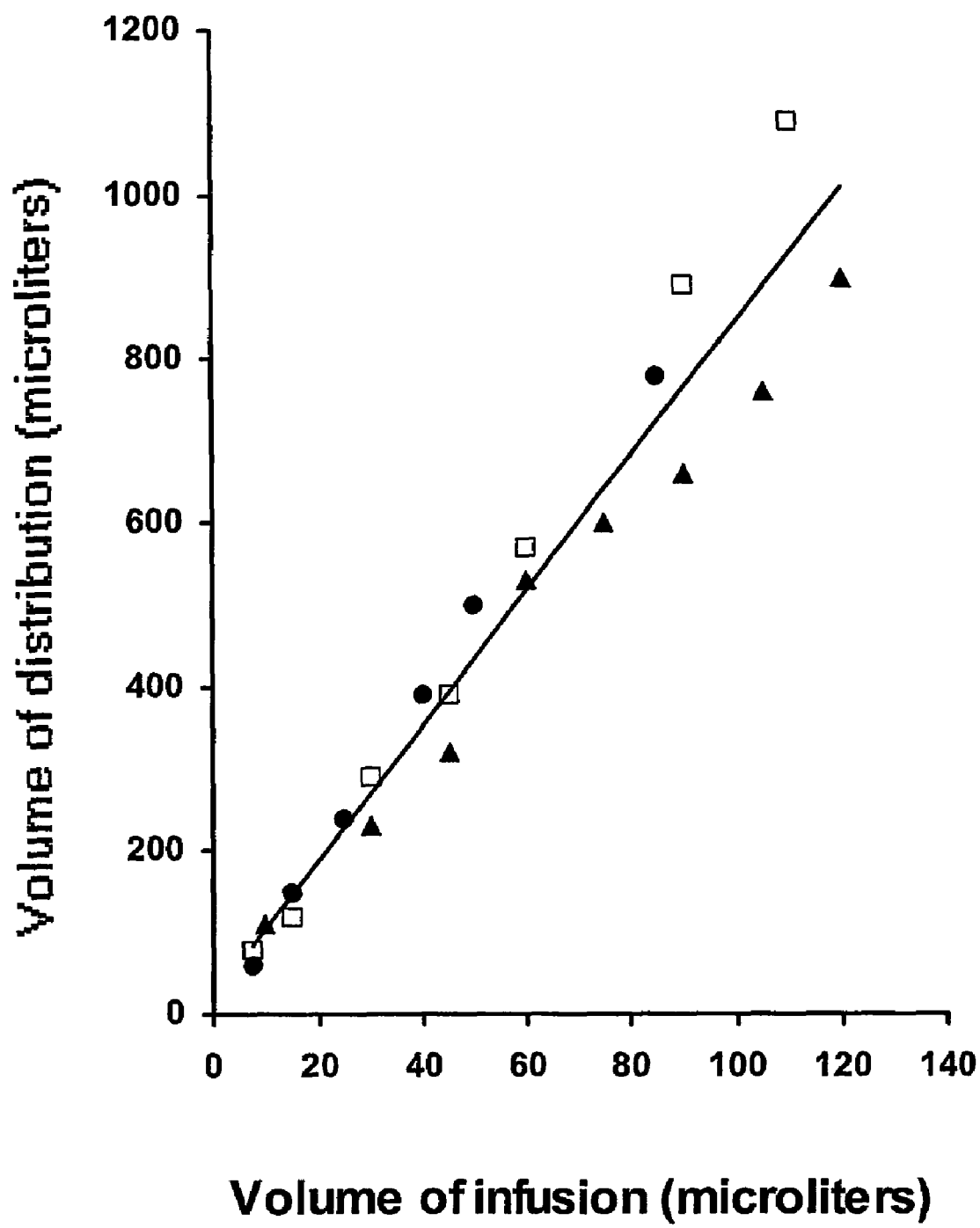
FIG. 4 is a graph showing the linear relationship ($R^2=0.94$) between volume of infusion (Vi) and volume of distribution (Vd) in primates infused with albumin-$(Gd-1B4M)_5$. The observed mean Vd:Vi ratio was 8.7±1.2 (mean±S.D.). Black circles, open squares and black triangles separately represent data derived from three animals.
Figure 5:
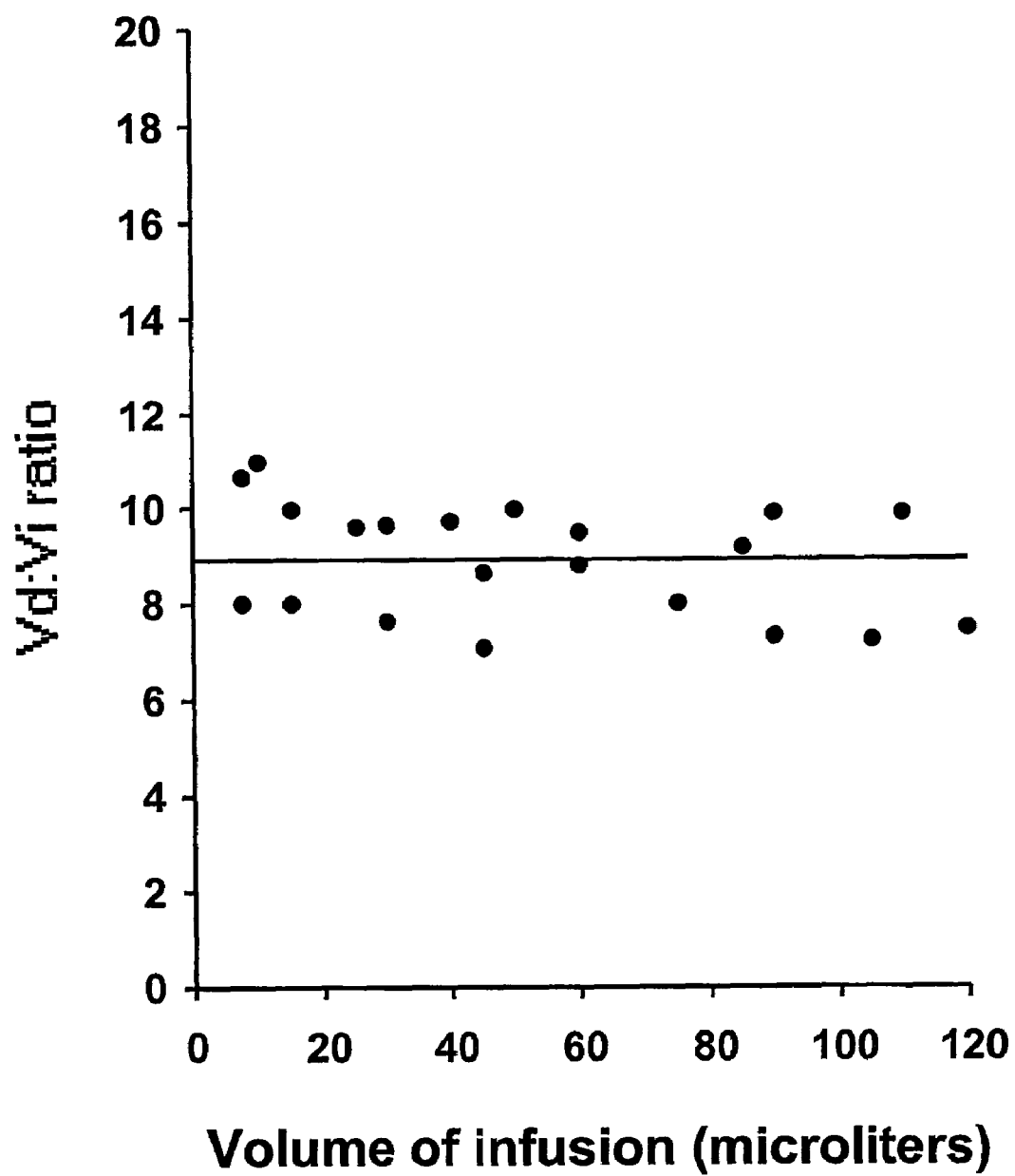
FIG. 5 is a graph showing that CED of albumin-$(Gd-1B4M)_5$ permitted correlation of predictable volume of distribution (Vd) (determined by real-time magnetic resonance imaging) to volume of infusion (Vi) ratio in the primates over various infusate volumes. Horizontal line represents the overall mean Vd:Vi ratio of 8.7±1.2 (mean±S.D.).
Figure 6:
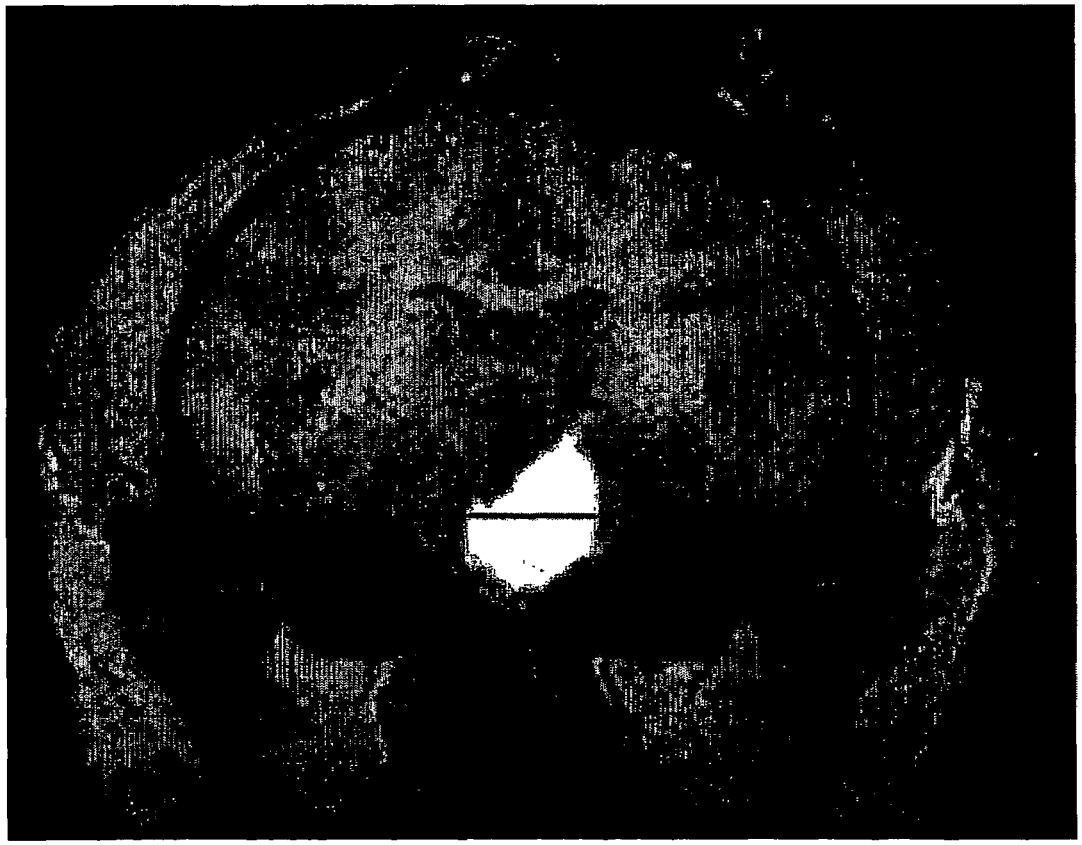
FIG. 6 is a coronal T1-wieghted magnetic resonance image in an animal infused with albumin-$(Gd-1B4M)_5$, showing the line across the infused region along which the image intensity was measured to generate the graph of FIG. 7.
Figure 7:
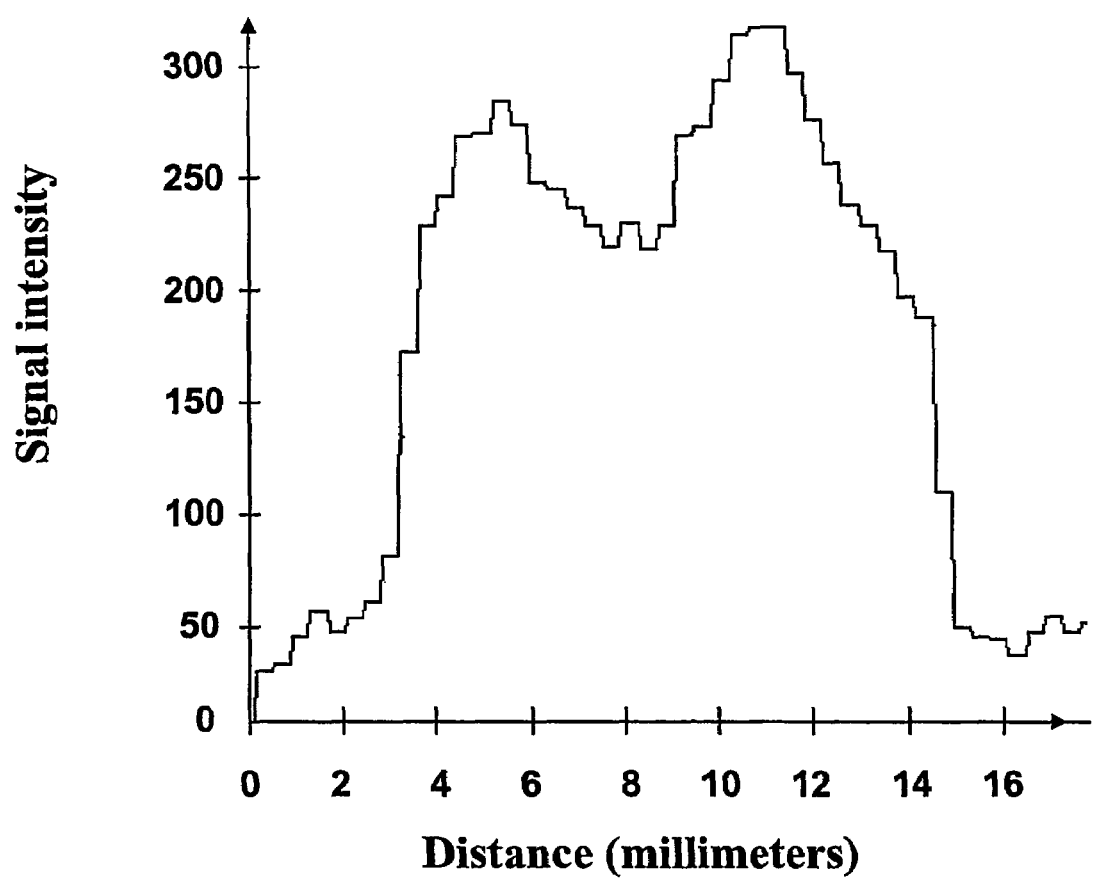
FIG. 7 is a line profile demonstrating the unexpectedly square-shaped intensity pattern (across the line shown in FIG. 6) indicative of relatively uniform concentration over the region of infusion, and a sharp drop in concentration at the edges of the infused region.

Real-time MRI of the Gd-albumin conjugate was performed (see FIG. 3). After placement of the infusion cannula, coronal T1-weighted MR-images were obtained to determine the precise location of the inner cannula (FIG. 3A). Once cannula placement was confirmed, infusions were started and T1-weighted MR-images (1.5 Tesla) (slice thickness 1 to 1.5 mm; 0 mm spacing) in 3 planes (sagittal, axial, and coronal) were obtained at approximately 20 to 40 minute intervals until the infusions were complete (FIG. 3 B-H). MR-images were analyzed on a Sun Workstation. Three-dimensional volumes of distribution (Vd) were calculated using as a threshold for segmentation the signal intensity value 2 standard deviations above the mean baseline signal from the surrounding non-infused anatomic region (FIGS. 4 and 5). To determine the homogeneity of the infusion over the infused Vd, line profiles were obtained through the center of the infusion as seen on coronal images (FIGS. 6 and 7). The validity and accuracy of these methods for calculating Vd and homogeneity from MR-imaging were confirmed using quantitative autoradiography (QAR) as described in Example 2 below.

Figure 8:
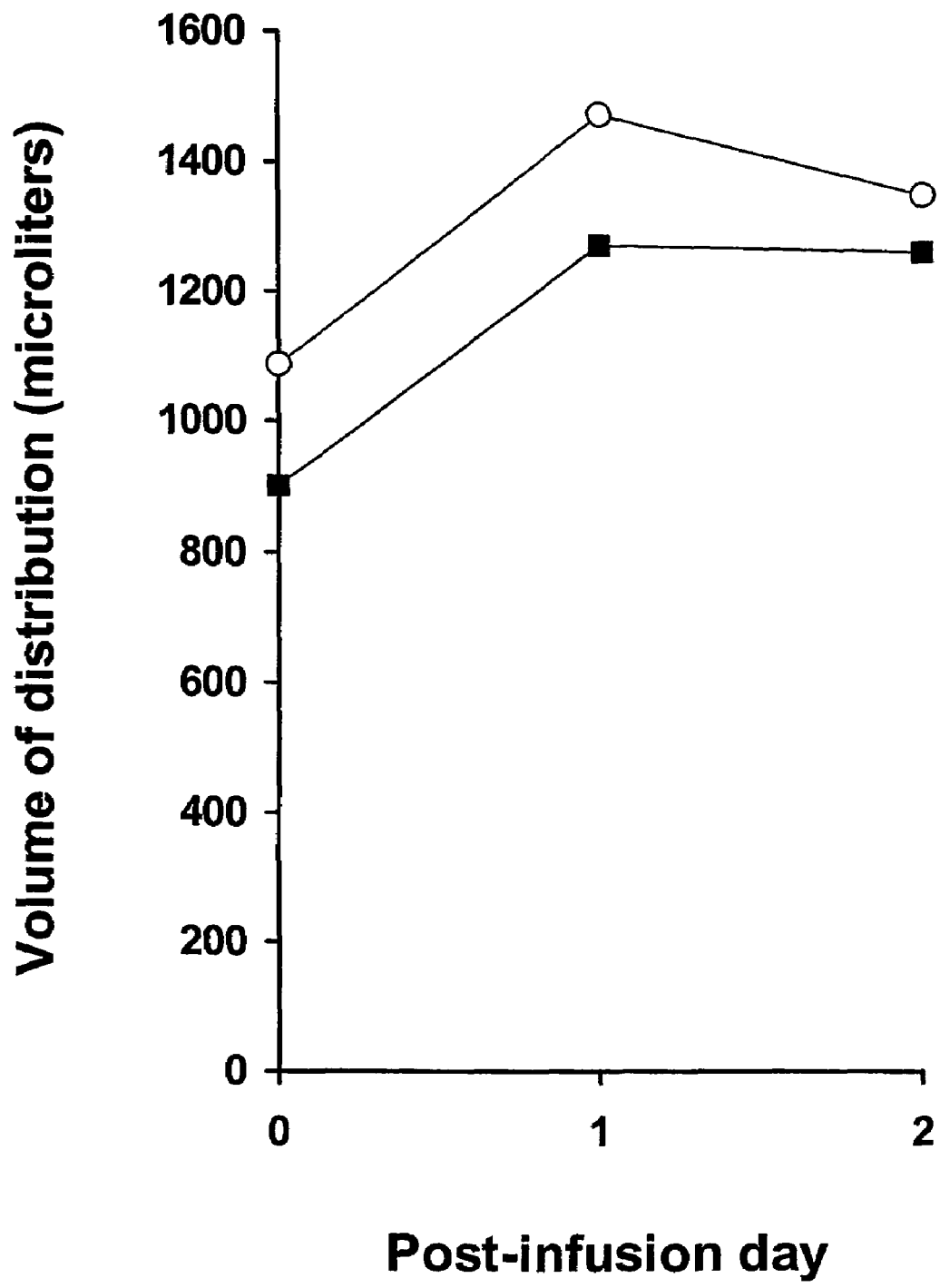
FIG. 8 is a graph showing the change in volume of distribution from immediately after infusion (Day 0) to more distant points in time in two different animals (open circles and black squares). The post-infusion day 1 increase in volume of distribution was 35% for Animal 2 and 41% for Animal 3.

Post-infusion imaging was also performed. Two primates underwent MR-imaging on days 0, 1, 2, 4, and 7 days after infusion of the Gd-albumin (see, for example, FIG. 8 showing 0, 1 and 2 day images). T1-weighted MR-images (1.5 Tesla) (slice thickness 1 mm; 0 mm spacing) in 3 planes (sagittal, axial, and coronal) were obtained. Three-dimensional Vd was calculated and homogeneity of the infusion was determined as described previously.

Primates were also observed daily for medical or neurologic difficulties over the study period (18 to 35 days). Each animal underwent postoperative videotaping within 48 hours of infusion completion and within 24 hours of euthanization.

After sacrifice, the animals' brains were perfused with phosphate buffered saline followed by 10% formalin. The brainstems were then cut coronally in 20-μm thick serial sections. Tissue sections through the entire brainsterm were histologically processed, and representative sections from each tissue block were stained with hematoxylin and eosin, Luxol fast blue, and Nissl. Immunohistochemistry for glial fibrillary acidic protein was performed.

Statistical analysis was performed on Stat View 5.0 (Abacus, Berkley, Calif.).

The HSA used in this example was obtained from Sigma (St. Louis, Mo.). The Gd (III) was obtained from Aldrich (Milwaukee, Wis.). The syringe pump (model 22) was obtained from Harvard Apparatus (S. Natick, Mass.). The Hamilton syringe, and PEEK tubing were obtained from Thompson Instruments (Springfield, Mass.). The silica cannulae and methylmethacrylate were obtained from Plastics One (Roanoke, Va.). The stereotactic frame (model 1504) was obtained from Kopf (Tujunga, Calif.). The Sun Work Station and software were purchased from Sun Microsystems, Inc. (Palo Alto, Calif.). The Stat View 5.0 software was purchased from Abacus Concepts (Berkeley, Calif.).

While Gd is an excellent imaging moiety for MRI, it is neurotoxic in its free state. Thus, a stable construct in which Gd is permanently bound to albumin (or other protein, dendrimer or therapeutic agent) is desirable. Following synthesis, the Gd-albumin conjugate was found to remain soluble, did not aggregate, and the Gd remained completely bound.

The rat experiments confirmed the safety of this compound (n=12). As described above, each rat underwent CED of 10 μl of Gd-bound albumin to the striatum unilaterally. None of the animals exhibited clinical deficits with extended observation (up to 60 days), and histologic analysis revealed normal tissue architecture with minimal gliosis limited to the immediate region surrounding the infusion cannula after infusion (n=12).

To demonstrate the feasibility of predictably distributing a large molecule in a clinically relevant volume to the brainstem while using MR-imaging to monitor its distribution in vivo, the brains of Rhesus primates (*Macaca mulatta*; n=3) (Table 1) were imaged during convective delivery of Gd-bound albumin to the pontine region.

TABLE 1

Convection-enhanced delivery of gadolinium-bound albumin to the primate brainstem.

| Animal Number | Total volume infused (μL) | Survival period (days) |
|---|---|---|
| 1 | 85 | 35 |
| 2 | 110 | 25 |
| 3 | 120 | 18 |

Figure 2:
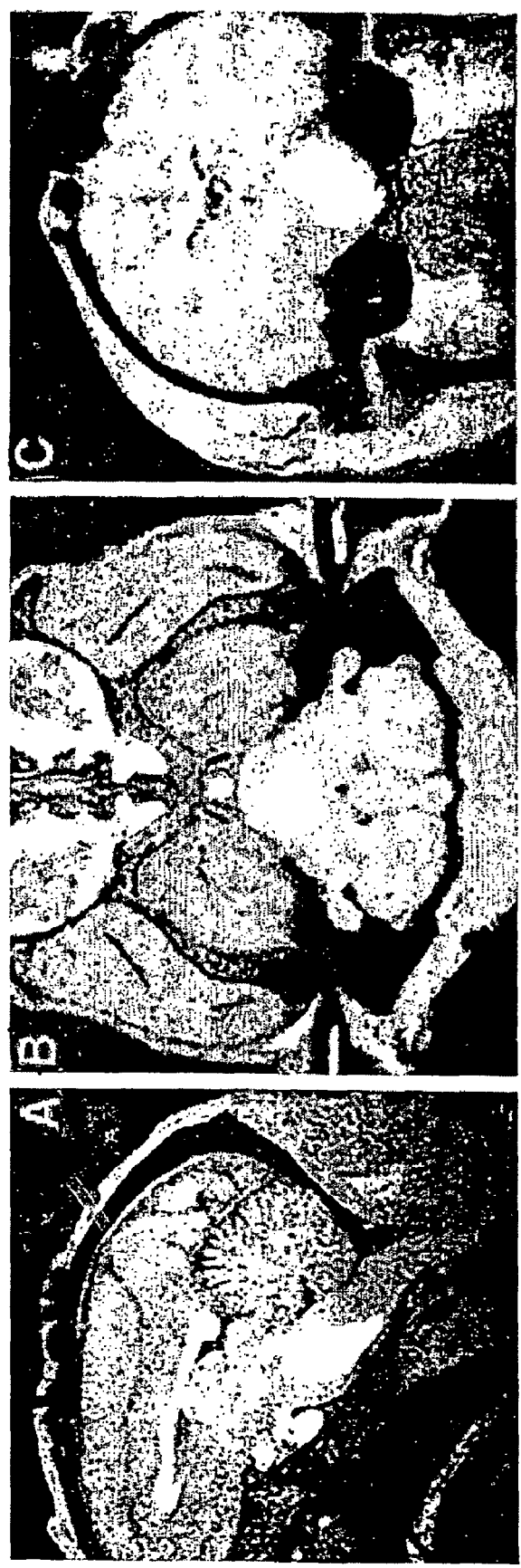
FIG. 2 is a series of T1-weighted magnetic resonance images obtained immediately after the completion of infusion of 120 µl of gadolinium-bound albumin into the pons. Sagittal (A), axial (B), and coronal (C) images through the brainstem region clearly demonstrate the region of infusion (white area), and near complete filling of the pons.

Real-time imaging (at 20 to 40 minute intervals) during infusate delivery showed that the anatomic region infused with Gd-bound albumin was clearly distinguishable from the surrounding non-infused tissue (FIG. 2). The pontine region surrounding the tip of the cannula steadily filled with the increasing volume of infusion (Vi) until the surrounding anatomic region was nearly filled with infusate (FIG. 3).

Volumetric analysis of the infused region at various points in time during the infusion revealed that the volume of distribution (Vd) of the Gd-bound albumin increased linearly with Vi ($R^2=0.94$) (FIG. 4), and the Vd:Vi ratio over the volumes infused was 8.7±1.2 (mean±S.D.) (FIGS. 4 and 5). The concentration of the delivered infusate in tissue was homogeneous. Cross-sectional line profiles through the infused region (FIG. 6) formed a square-shaped pattern (FIG. 7, indicative of a relatively uniform concentration over the region with a sharp gradient drop-off at the edges (FIG. 6). Hence, the observed image represents uniform delivery of an infusate to a well defined region and demonstrates that the image may be used to determine when a therapeutic agent has been uniformly delivered to substantially only the targeted tissue, either directly (for example, where the tracer is attached to the therapeutic agent) or through some correlation between the observed image volume and the volume in which the therapeutic agent is distributed (for example, when the tracer and therapeutic agent are not linked and the mobilities of the tracer and the therapeutic agent are dissimilar).

To determine the characteristics of the infusion at points in time after completion of the infusion, post-infusion MRI (at days 1, 2, 4, and 7 after infusion; n=2) was performed. MRI of the infused region revealed an increase in Vd (compared to the Vd immediately after the completion of the infusion) starting at post-infusion day 1 (FIG. 8). The post-infusion day 1 increase in Vd was 35% for Animal 2 and 41% for Animal 3. These increases remained relatively stable until the intensity of the Gd-albumin conjugate faded to that of surrounding normal tissues (by post-infusion day 7, not shown). Cross-sectional line profiles through the infused region on post-infusion MR-imaging (post-infusion days 1 and 2) continued to have a square-shaped pattern (data not shown), indicative of a continued uniform concentration in the region of infusion.

As mentioned above, the safety and potential for tissue toxicity of CED of Gd-albumin conjugates in the brainstem was assessed. Infused primates were followed with serial clinical examinations (up to 35 days), and underwent histologic analysis of the infused region upon euthanization. No animals had a detectable neurologic deficit after infusion throughout the observation period. Gross examination of the brain and brainstem revealed normal weight and no evidence of edema. Brainstem sections stained with Luxol fast blue, Nissl's, and hematoxylin and eosin, revealed normal tissue architecture. Glial fibrillary acidic protein staining revealed minimal gliosis limited to the region immediately surrounding the cannula tract.

As described in the background, CED delivery relies on bulk flow to distribute substances within the interstitial spaces of the CNS. Unlike intraventricular delivery, which relies on diffusion, convection is not limited by the infusate's molecular weight, concentration, or diffusivity. Moreover, because convective delivery directly distributes molecules within the parenchyma it can be used to target selected regions of the CNS in a manner that bypasses the blood-brainstem barrier, which limits the distribution and efficacy of systemically-delivered agents. Previous studies have shown that the properties of convective delivery can be used to distribute small and large molecules homogeneously over clinically relevant volumes in a safe and reproducible manner within the spinal cord and brain. This Example demonstrates that MRI may be combined with CED to provide a novel method for drug-delivery that includes in vivo real-time monitoring of infusate distribution within the brainstem to achieve delivery to substantially only the target tissue.

Real-time MR-imaging revealed that the Vd increased linearly ($R^2$=0.94) with increasing Vi, and the overall Vd:Vi ratio was 8.7±1.2. This ratio reflects the distribution of substances within the interstitial spaces, and is significantly higher than previous studies that used CED of similar substances within the grey matter of the brain (Vd:Vi; 5.0±0.2) and white matter tracts of the spinal cord (Vd:Vi; 4.4±0.5). This indicates that the interstitial space of the brainstem is small compared to these other regions of the CNS, as distribution is inversely related to the size of the extracellular space of the infused region. A reduction of interstitial space may be a result of the densely packed white matter tracts that exist in this region of the CNS. By taking advantage of the tight arrangement of fibers in this region and the large Vd:Vi ratio, clinically relevant portions of tissue in this region were rapidly filled.

MR-imaging revealed expansion of Vd on post-infusion day 1, and stabilization of the expanded Vd in subsequent imaging studies (infusate visible through post-infusion day 4). Apparently, convective distribution of the infusate may continue after completion of infusate delivery, as the expansion cannot be explained by diffusive forces for the large molecular weight albumin tracer. Furthermore, the expansion of distribution apparently continues only until the pressure gradient that drives infusate dissipates, since the expansion observed in the first post-infusion images remained stable at later times.

The distribution of the infusate was homogeneous. Analysis of infusate intensity on MR-imaging revealed uniformity and a sharp drop-off at the edges of the infused region. This square-shaped concentration profile was maintained throughout the period of strong visible enhancement on post-infusion MR-imaging (through post-infusion day 2) (FIG. 7). This underscores the ability of the disclosed technique to provide controllable distribution of molecules in a highly uniform concentration substantially within the targeted region, maintain this uniformity over an extended period of time (with this tracer compound), and avoid the non-targeted, heterogeneous delivery of compounds associated with systemic or intrathecal delivery. In other words, controllable delivery to substantially only the target tissue is possible.

It is believed that CED of macromolecules to the brainstem followed by MRI has widespread application in the investigation and treatment of brainstem conditions. One example of a specific disorder that may be treated with CED of therapeutic agents is diffuse pontine gliomas. These neoplasms primarily affect young children, and are uniformly fatal because they are not surgically resectable, and chemotherapeutic agents cannot be delivered in a successful manner using conventional techniques due to the limitations of these methods. CED coupled with MRI (or other imaging techniques) allows for the direct and predictable delivery of therapeutic agents to these or other lesions of the brainstem. The demonstrated ability to co-infuse surrogate imaging tracers or directly label therapeutic compounds allows for real-time visualization of drug delivery into this and other regions of the CNS. Thus, regional delivery employing CED in this manner should prove useful in studying and treating a variety of CNS disorders.

Example 2

Convection-enhanced delivery (CED) allows distribution of therapeutic agents to large volumes of brain at relatively uniform concentrations. This mode of drug delivery offers great potential for treatment of many neurological disorders, including brain tumors, neurodegenerative diseases and seizure disorders. Treatment efficacy and prevention of unwanted toxicity using the CED approach, however, depend on the infused therapeutic agent being distributed in a targeted manner to the targeted region, while mmnizing delivery to non-target tissue, and in concentrations that are in the therapeutic range. As demonstrated above in Example 1, MRI may be used to visualize the process of CED.

In this Example, accurate and uniform delivery of therapeutic agents during CED is confirmed and monitored in real time with the noninvasive imaging technique X-ray computed tomography (CT). The CT technique is also compared to the MRI technique. Tracers comprising albumin conjugated to iopanoic acid for CT and a gadolinium-metal chelate for MRI were prepared and were investigated for their usefulness as surrogate tracers during convective distribution of a macromolecule. The tracers were infused in the cerebral hemispheres of monkeys, and the volumes of distribution using CT and MRI were measured. The distribution volumes measured by imaging were compared with the tissue volumes measured by quantitative autoradiography (QAR) using $^{14}$C-albumin co-infused with the tracers. The correlation of concentration of the tracer in brain homogenate standards and CT Hounsfeld units also demonstrate that CT may be used to quantify infusate concentration during CED. Similarly, the usefulness of MRI for quantifying infusate concentration in tissue was demonstrated. The long-term effects of the surrogate tracer for CT(iopanoic acid-albumin) on animal behavior, tissue histology, and parenchymal toxicity after cerebral infusion were also established.

The examples described below demonstrate that controlled and predictable distribution of a macromolecule to clinically significant volumes in the brain is possible using CED in combination with imaging, such as serial imaging. They also confirm that the spatial dimensions of the tissue distribution can be accurately defined in vivo during infusion using surrogate tracers and conventional imaging techniques, and show that the use of radiographic surrogate tracers is a practical and safe method for establishing treatment volumes during high-flow interstitial microinfusion of the CNS. The disclosed method may be used to monitor, in real time, the geometry of the distributed volume and to reveal low tissue resistance and preferential flow along fiber tracts and backflow associated with rapid infusion rates and larger catheter sizes, both of which can produce nonuniform delivery of a therapeutic agent and delivery outside of the targeted tissue. Use of a tracer to noninvasively determine in vivo tissue concentrations also provides important information that may be used to establish dose-dependent efficacy and neurotoxicity.

Iopanoic acid (an X-ray imaging moiety) was conjugated to BSA (IPA-BSA) and HSA (IP-HSA) (Sigma Chemical Co.) by slow addition of the N-hydroxysulfosuccinimide active ester of iopanoic acid in DMSO (1.5 mL solution of 140 mg/mL) to 10 ml of BSA (10 mg/mL in 0.07M HEPES, pH 8.5). After mixing for approximately 5 h at room temperature, the precipitate was removed by centrifugation. The supernatant was filtered (0.22-μM), purified by diafiltration against phosphate buffered saline (PBS) (pH 7.2, 0.15 M NaCl) using a chamber fitted with a YM10 membrane (Amicon, Millipore Corp., Bedford, Mass.), and concentrated by centrifugation (10 K Centricon) to approximately 70 mg/ml with a typical IP:albumin ratio of 40-45 (determined by measuring UV absorbancies at 315 nm vs. 280 nm).

An albumin-Gd-DTPA conjugate was synthesized as previously described in Ogan et al, "Albumin labeled with Gd-DTPA: An intravascular contrast-enhancing agent for magnetic resonance blood pool imaging: preparation and characterization," Invest Radiol 22:665-671 (1987) [published erratum appears in Invest Radiol 1988 December;23(12):961]. This preparation had 26 DTPA ligands linked to each albumin molecule and had a calculated MW of 78 kDa.

The putamen in six adult rhesus monkeys (8-10 kg) was targeted for unilateral convection of IPA-BSA (n=3) or albumin-Gd-DTPA (n=3). Anesthesia was induced with ketamine (10 mg/kg), xylazine (0.5 mg/kg), and thiopental sodium (1 mg/kg). The animals were secured in a monkey stereotactic frame (Kopf Instruments, Tujunga, Calif.). A Hamilton 32-gauge metal blunt tip needle connected to a 250 μl Hamilton syringe (Thompson Instruments, Chantilly, Va.) was stereotactically inserted in the center of the right putamen (anteroposterior 15.5 mm, mediolateral 12 mm and dorsoventral 24.5 mm relative to the tympanic canals and the mid-sagittal sinus)[15]. After a delay of 90 minutes, the infusion was begun at 1.0 μl/min.

For CT, 130 μl, 200 μl and 235 μl of the tracer IPA-BSA/$^{14}$C-BSA mixture (35-55 Iopanoic Acid/BSA, 61.3-80.4 mg/ml $^{14}$C-BSA) was infused. For MRI, 130 μl, 185 μl and 230 μl of a mixture of albumin-Gd-DTPA (0.76 mM Gd(III), 0.03 mM HSA) and $^{14}$C-BSA were infused. Following infusion, the animals were imaged by CT or MRI, and immediately afterward were euthanized by pentothal overdose. The whole brains were removed and stored at −80° C. for one week before analysis.

CT imaging was performed on a Helical CT unit (General Electric Medical Systems, Milwaukee, Wis.). IPA-BSA was imaged using a DFOV of 13.0-19.0 cm, 120 kV, 200-280 mA, a slice thickness of 3.0 mm, and a 512 Matrix.

MRI was performed on a 1.5-Tesla unit (General Electric Medical Systems, Milwaukee, Wis.). Coronal and axial images were obtained at a TR/TE ratio of 15.4/6.3 msec, a FOV of 10×10 mm, a 1.0 mm slice thickness with a 0.0 mm spacing and a 256×192/4 nex matrix.

$^{14}$C-methylated BSA (American Radiolabeled Chemicals, Inc., St Louis, Mo.) was co-infused with each tracer. After sacrifice, the brain was frozen at −70° C., 20-μm thick cryostat sections on collagen-coated glass slides were obtained, and exposed on a phosphor imaging plate (Fuji Medical Systems, Stamford, Conn.) along with $^{14}$C plastic standards (American Radiolabeled Chemicals, Inc., St. Louis, Mo.) at room temperature. After one week, the imaging plate was digitally scanned in the FujiFilm BAS5000 Bio-imaging Analyzer. The images were calibrated using a previously established correlation between $^{14}$C plastic standards and 20-μm rat brain sections containing $^{14}$C. The tissue volume of distribution (Tvd) was defined as the volume containing >10% of the peak radioactivity at the infusion site. The areas of sections encompassing the perfused region were summed and multiplied by the spacing between sections. Profiles of the $^{14}$C-BSA were obtained across the infusion in sections corresponding to the center of the infusion.

CT and MRI images were analyzed in the MEDx software package (Sensor Systems, Inc., Sterling, Va.) running on a Sun workstation (Sun Microsystems, Inc., Palo Alto, Calif.). Three-dimensional (3D) volumes of distribution, $V_d$, were defined as the ratio of the volume of perfused tissue divided by the volume of infusate. These were measured by volume segmentation using two different thresholds. $V_d(1)$ was calculated as the volumes of distribution from CT and MRI containing at least 10% of the total increase in signal intensity due to the addition of contrast agent. A rectangular region of interest (ROI) over the infusion area was defined and in the corresponding site in the contralateral hemisphere, and the perfused maximal signal intensity (peak) and the unperfused maximal signal intensity (background) was measured. A signal intensity of baseline plus 10% of this difference was used to obtain the threshold value for volume segmentation. To define a simpler technique to calculate the imaged volume, $V_d(2)$ was calculated using, as the threshold for segmentation, the signal intensity value that was 2 standard deviations above the mean baseline signal intensity. To determine the homogeneity of the contrast in the volume of distribution, line profiles were obtained through the center of the infusion as seen on coronal images.

In vitro standards were prepared as follows. Rat brain was homogenized in PBS (1:1 v/v) and 2% percent gelatin. $^{14}$C-albumin and ioxilan (Oxilan-R) in various concentrations were added. The standards were frozen overnight at −80° C., scanned using CT and sectioned at 20 μm. Slides were scanned in the phosphor imaging system as described above. Using a 3×3-voxel grid overlaid onto the CT image and the corresponding QAR image, matched pairs of CT Hounsfeld and QAR signal density values at each concentration were generated and a regression analysis was performed.

Safety and toxicity of the CT tracer was investigated in Sprague-Dawley rats (n=3 per group) that were infused in a stereotactic frame (Kopf Instruments, Tujunga, Calif.) with 5 μl IPA-HSA (81.3 mg/ml, 35-45 IPA per HSA) at 0.5 μl/min in the putamen (A 0.5 mm, L 3.5 mm, and D 5.5 mm with respect to bregma and dura), and sacrificed after 7, 14 and 39 days or when signs of toxicity were present. Animals were examined daily for behavioral evidence of toxicity. At the time of sacrifice, brains were harvested, frozen, sectioned at 20 μm and stained with hematoxylin and eosin and anti-glial fibrillary acidic protein antibody (GFAP).

Figure 9:
FIG. 9 shows axial (top) and coronal (bottom) CT images of infused iopanoic acid-BSA. Discrete volumes are located in and throughout the targeted putamen. The shape of the infusions follows anatomical contours, with some spread into the adjacent white matter. Signal intensity is relatively uniform at, a-130 µl infusion, b-200 µl infusion, and c-235 µl infusion. All infusions were performed at 1 µl/min.
Figure 10:
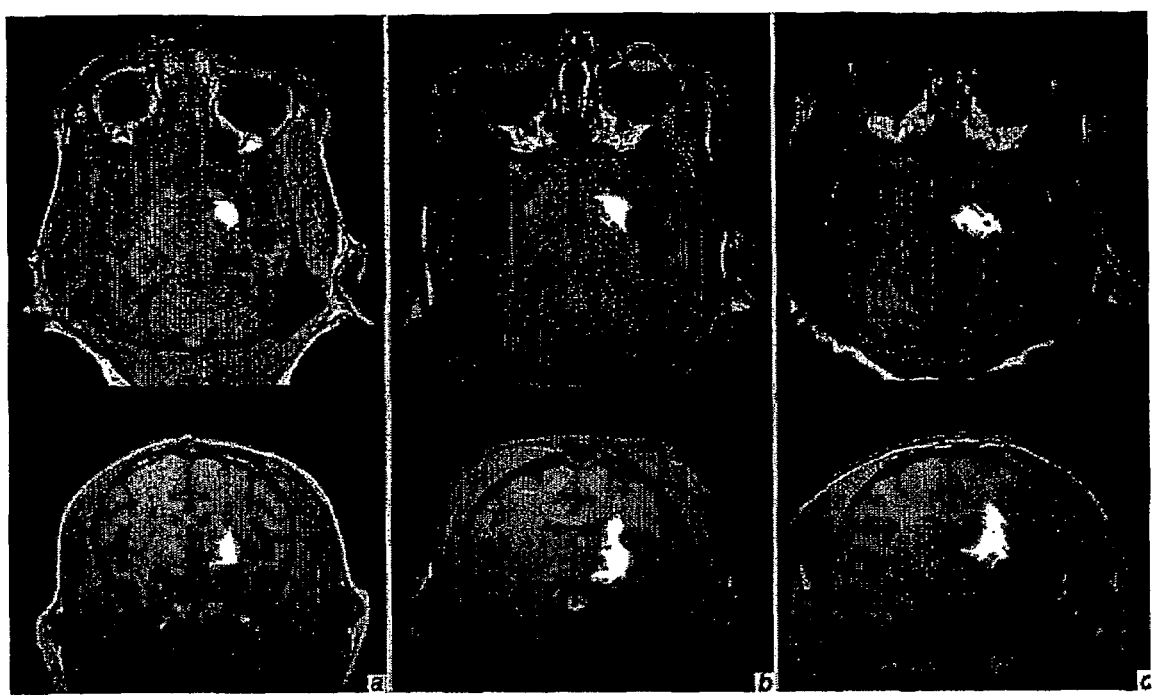
FIG. 10 shows axial (top) and coronal (bottom) MRI images after infusion of gadollnium-DTPA:HSA. With increased image resolution, distributions within the putamen are clearly seen. At larger volumes of infusion the surrounding white matter is perfused. Signal intensity is relatively uniform throughout at a-130 µl infusion, b-185 µl infusion, and c-230 µl infusion. All infusions were performed at 1 µl/min.
Figure 11:
FIG. 11 shows coronal MRI images showing that the perfused area of FIG. 10 does not extend into optic tract. In the two animals shown, the infusion reached the inferior aspect of the putamen and surrounded, but did not penetrate, the optic tract (arrows).
Figure 12:
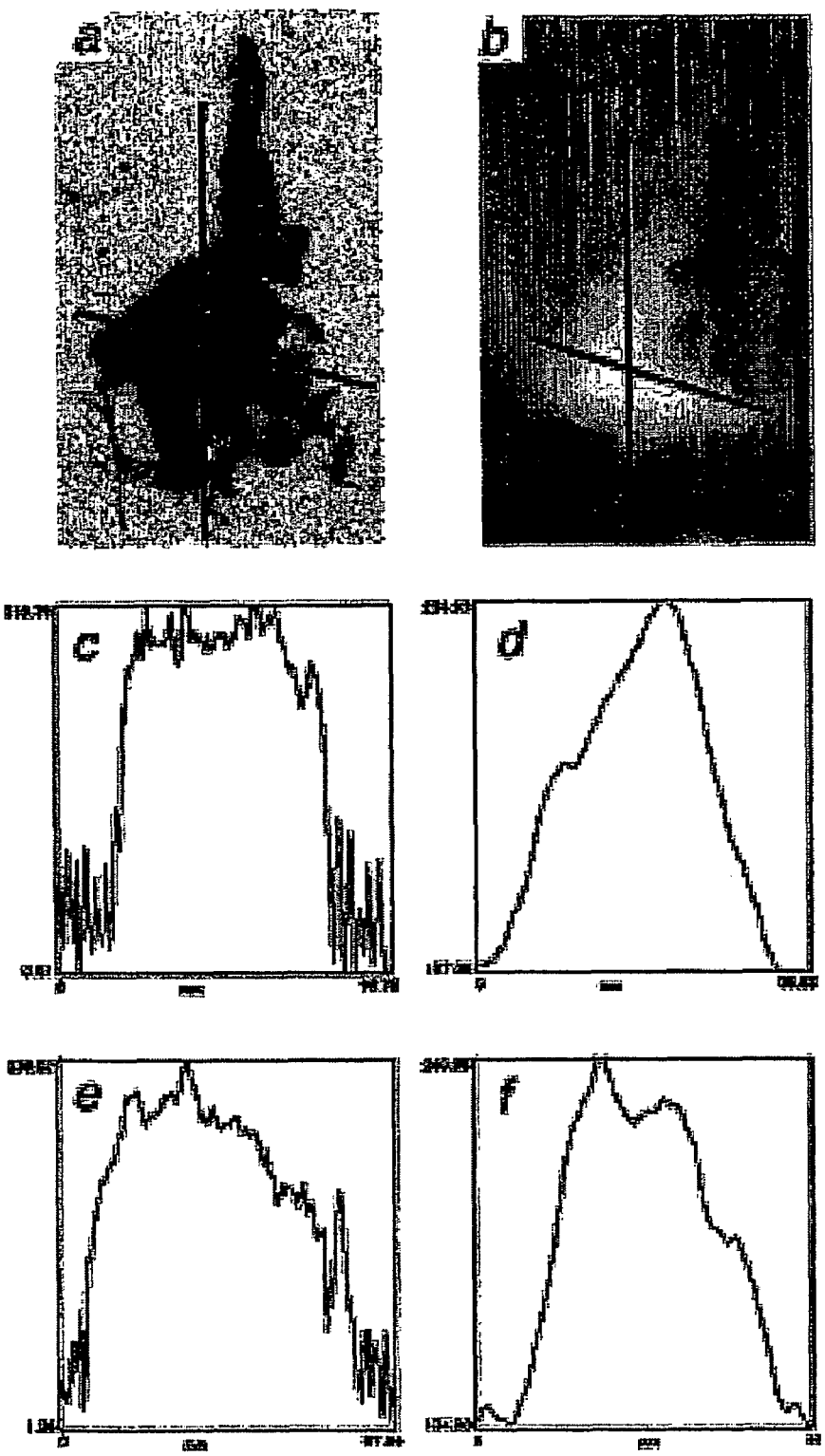
FIG. 12 shows the uniform distribution of iopanoic acid: albumin surrogate tracer on CT. Note comparable shapes of the perfused regions on QAR and CT images (a and b). Vertical (c) and horizontal (e) line profiles of QAR (a) section shows typical pattern, which is characterized by flat baseline, steep slope at the edge, and plateau of peak signal intensity within the area of infusion, and is indicative of uniform concentration of $^{14}C$-albumin in the perfused area. Similar line profiles (d,f) through the CT image (b) also show the steep gradient at the edges of the perfused region.
Figure 13:
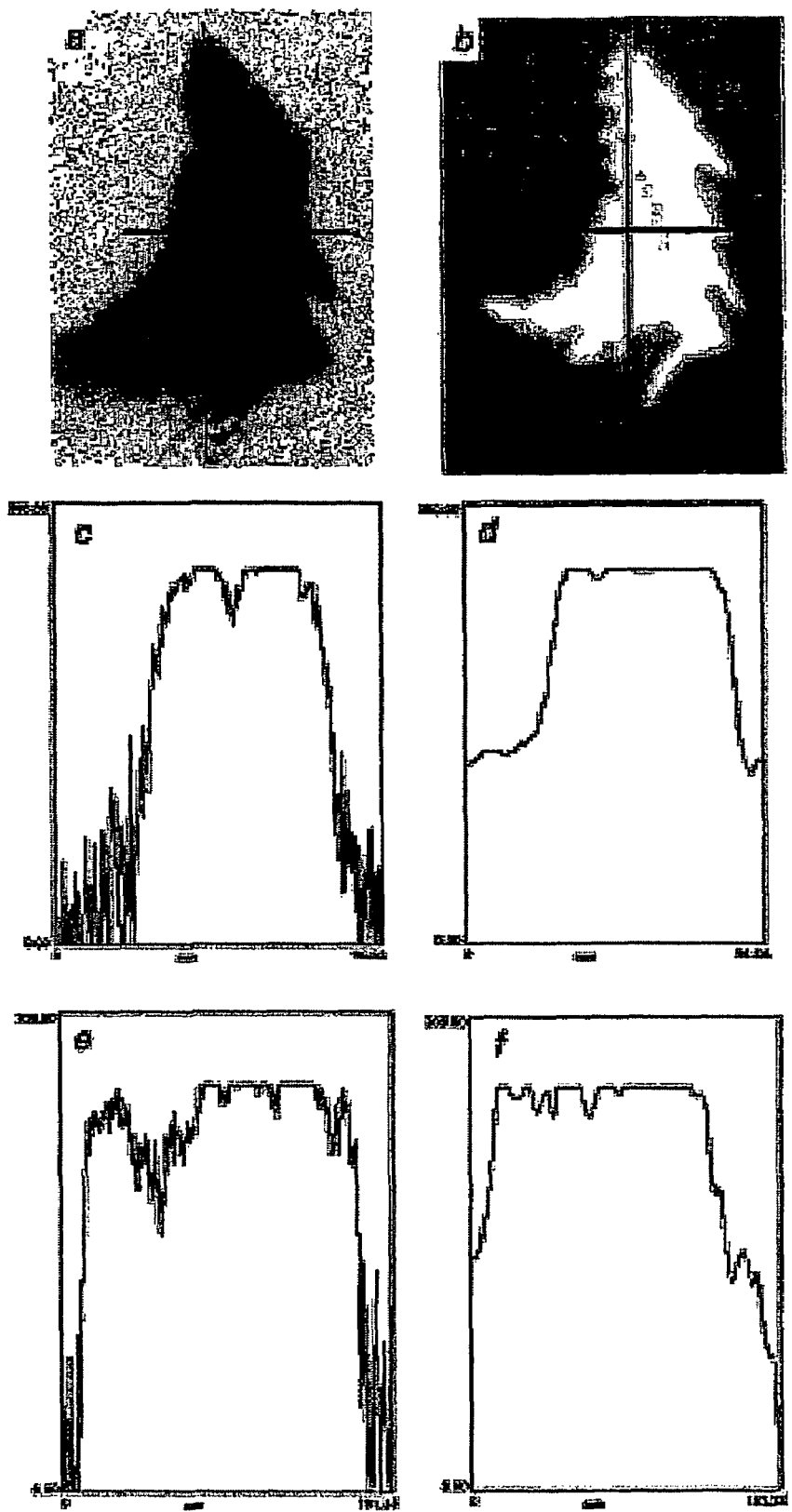
FIG. 13 shows the uniform distribution of gadolinium: albumin surrogate tracer in a targeted brain region. Vertical (e,f) and horizontal (c,d) line profiles of matching QAR (a) and MRI (b) images show typical square wave pattern, indicative of the uniform distribution of $^{14}C$-albumin and gadolinium-albumin tracer in the perfused area. Note the similar shapes of the line profiles for the two imaging modalities. The vertical axis has been truncated as shown.

To assess the appearance of the surrogate tracers using CT or MRI scanning, animals were scanned immediately after CED of the tracers to the putamen. The perfused areas were clearly visible on CT and MRI following the infusions (FIGS. 9 and 10). The shape of the infusion followed the anatomic boundary of the basal ganglia, with some spread into the adjacent white matter of the corona radiata after larger volumes of infusion. The infusions did not extend into the contiguous optic tract (FIG. 11). The perfused regions, particularly those on MRI, had relatively uniform distribution profiles and steep concentration gradients at the interface between the infusion volume and surrounding parenchyma (FIG. 13). The anatomic resolution was superior with MRI, with which distribution in the nuclei and traversing white matter tracts could be identified. There was more variability of signal intensity within the CT volumes (FIG. 12), indicating that it should be possible to increase the concentration of IPA:BSA to better differentiate between unperfused and perfused brain.

To demonstrate that the imaged volume accurately reflected the volume distributed in the tissue, the imaged volumes were compared to those measured by quantitative autoradiography (QAR). First, the volume of radioactive perfusion on QAR was defined as that which contained at least 10% of the peak radioactivity in the perfused areas. Next, the volumes of distribution from CT and MRI were calculated based on those portions of the image which contained at least 10% of the total increase in signal intensity due to the addition of contrast agent [$V_d(1)$]. Volumes of distribution [$V_d(2)$] were also calculated by counting only those voxels that had signal intensity values greater than two standard deviations above the mean voxel intensity in the unperfused brain. Mean $V_d(1)$ and $V_d(2)$ for the CT tracer were 3.44±0.74 and 4.51±1.31, respectively, compared to 4.26±0.24 using the QAR results. Mean Vd(1) and Vd(2) for the MRI tracer were 2.55±0.44 and 2.62±0.28, respectively, compared to the tissue distribution of 3.86±1.05 measured by QAR.

Uniform distribution was also demonstrated. The uniformity of the concentrations in the perfused regions was similar between the QAR measurements and those derived from CT and MRI. Line profiles through the cross-sectional areas (FIGS. 12 and 13) show a relatively uniform concentration in the perfused region with steep gradients at its edges, again demonstrating the ability of the disclosed method to deliver infusates to substantially only the target tissue.

Figure 14:
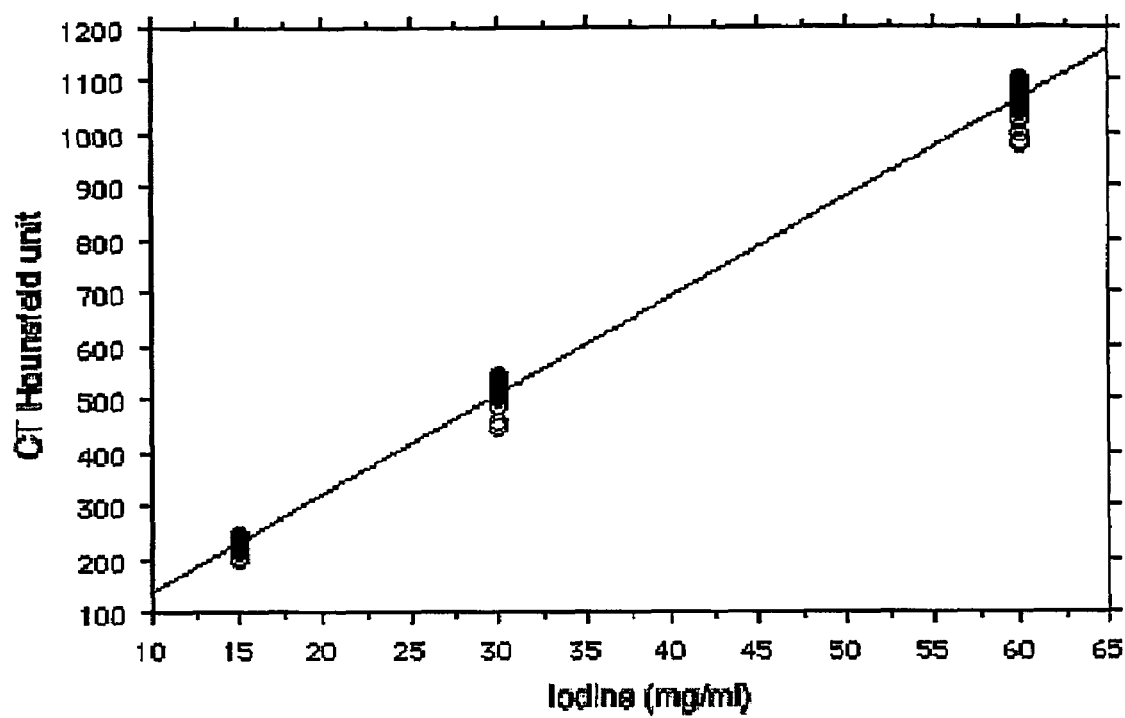
FIG. 14 is a graph showing the correlation of iodine concentration and CT signal intensity. Using brain homogenate in vitro standards containing both the $^{14}C$-labeled albumin and the surrogate tracer, the correlation between CT Hounsfeld units and radioactivity was linear with an $r^2$ value exceeding 0.995.

To demonstrate that the tissue concentration of the albumin (and therapeutic agents) can be predicted on the basis of CT images, the relationship between the Hounsfeld units on CT imaging and the concentration of $^{14}C$-labeled albumin was assessed. Using brain homogenate in vitro standards containing both the $^{14}C$-labeled albumin and the surrogate tracer, the correlation between CT Hounsfeld units and radioactivity was linear with an $r^2$ value exceeding 0.995 (FIG. 14). This graph demonstrates that if the relative concentration of a therapeutic agent and a CT tracer are known, the concentration of the therapeutic agent in a particular portion of the perfused tissue may be determined from the image intensity (in CT Hounsfeld units) of the tracer in that portion.

The relative lack of neurotoxicity of the iopanoic acid-albumin surrogate tracer was demonstrated after a single convective infusion in the rat brain. There were no behavioral changes at 7, 14 and 39 days after infusion. In autopsied animals, needle track marks were visible at 7 and 14 days, but had disappeared at 39 days. Edema was noted at the infusion site in ⅓ animals sacrificed after 7 days but was completely resolved by 14 days. No hemorrhage occurred at the infusion site. Enhanced GFAP staining was minimal at the edge of the infusion and along the needle track at 14 days, but there was no difference in GFAP staining between the treated and untreated hemispheres at 39 days. Particularly, there was no evidence of reactive astrocytic proliferation surrounding the infused area.

Predictable and controllable distribution and visualization of a macromolecule delivered to clinically significant volumes in the primate brain using convection was demonstrated. After co-infusion of a mixture of $^{14}C$-labeled albumin and albumin tagged for visualization on CT or MRI, the CT and MRI images showed discrete volumes of contrast perfusion in the striatum, and the geometry of the perfused regions corresponded closely with the distribution that was evident from corresponding QAR images demonstrating delivery to substantially only the target tissue may be acheived through monitoring the infusion with an imaging technique. The distribution of tissue perfusion covered the targeted region (the striatum). At the larger infusion volumes (230 μL and 235 μL), flow into adjoining white matter tracts was detected by both imaging techniques, but no flow inferiorly into the optic tract was detected on MRI. The radiographic volume of distribution obtained by CT was similar to the volume obtained by QAR for all volumes tested, while the distribution volumes measured by MRI were consistently smaller. Thus, it may be desirable to cease delivery at an earlier time when following an infusion using the MRI technique. Regardless, once a correlation between the distribution observed in MRI and the distribution observed by QAR is established, the correlation may be used to determine when an infusate has reached the targeted tissue. In addition, these results demonstrate that the uniform distribution shown in the CT/MRI line profiles correlates with the uniform concentration distribution shown by QAR, and that the CT/MRI images themselves may be used to monitor concentration of therapeutic agents during CED.

Delivery of therapeutic agents to large targeted volumes (and substantially only to those targeted volumes) of the brain offers great potential for treatment of many neurological disorders, including neurodegenerative diseases, seizure disorders, and brain tumors. For diseases such as Parkinson's disease and mesial temporal sclerosis, in which volumes of normal human putamen, caudate, amygdala, and hippocampus range from 1.5 to 7.5 ml, potential target areas should be completely perfused by infusing 0.4 ml over a 7 hour period, or 1.9 ml over a course of 32 hours, assuming a flow rate of 1 μgl/min and a volume of distribution equal to four. While intratumoral delivery of macromolecules has been performed safely in humans with high-grade astrocytomas, the diffusely infiltrating nature of astrocytomas requires therapy targeting large areas of brain, perhaps entire hemispheres. This can theoretically be accomplished by combining the anatomic distribution of multiple infusion catheters to effectively target a much larger perfused area. In such a situation, the disclosed methods that incorporate imaging can be used to follow delivery and help confirm that all areas are perfused, and avoid some areas receiving multiple doses from the multiple catheters.

To demonstrate the effectiveness of any agent using convection, the concentration of the agent is desirably confirmed to be in the therapeutic range. Given the uniform concentrations after convective delivery and the linear correlation between iodine concentration and Hounsfeld units, it is straightforward to use CT to measure the concentration of tracer concentration in each voxel of tissue, which of course may be correlated with the therapeutic agent's concentration. However, the intensity of tissue enhancement (for exaniple, by Gd-DTPA) may not always be a completely accurate predictor of concentration, because the relationship of gadolinium concentration to the degree of enhancement is complex and bimodal, with signal intensity rising to a peak and then falling as gadolinium concentration increases (see, Wang et al, "Magnetic resonance imaging contrast enhancement versus tissue gadolinium concentration," *Invest Radiol* 25 Suppl 1:S44-45 (1990)). However, in practice, as here, the concentration range of gadolinium during convective delivery was limited, and within this range an approximately linear relationship between gadolinium concentration and signal intensity is expected.

An advantage of direct regional delivery is the ability to target specific anatomical areas of the brain, as well as the potential of targeting therapy to specific cell populations. Furthermore, structural tissue differences (gray versus adjacent white matter) shape the distribution achieved with convection to the non-spherical anatomical structures of interest. However, even with optimal anatomical targeting using modern stereotactic neurosurgical techniques, anisotropy of the brain may lead to convective distribution of drug into areas outside the intended target. It is also possible that leakage of drug back along the needle track with high infusion rates (backflow) may occur. Inadvertent delivery of drug into the CSF may occur if retrograde movement of drug reaches the subarachnoid space. Monitoring distribution of tracer (such as surrogate tracers) during drug infusion permits identification of unexpected distribution or retrograde leakage along the catheter, permitting corrective measures such as adjusting the infusion rate or repositioning the catheter tip. For these reasons, a radiographic or magnetic resonance method to follow the distribution of perfusion during convection, so that the infusion parameters can be optimized to perfuse only the targeted region, is helpful. Additionally, measurement of distribution volumes in different regions of brain or tumor provides useful data to model anisotropy of the brain and its influence on drug distribution during CED. Such measurements of distribution volumes are subsequently used to predict patters of CED drub delivery in subjects who are receiving therapy.

In principle, convective delivery of macromolecules which do not interact with cell surfaces or the extracellular matrix will travel within the extravascular space independent of molecular weight and will be distributed extensively at a uniform tissue concentration. The disappearance of the molecule over time represents the combined effects of capillary re-uptake, biological degradation, and loss by natural convection and slow diffusion. The distribution measured by the co-infusion of surrogate tracer with a therapeutic macromolecule, if both are similar in size, represent a reliable indication of the distribution of that macromolecule. However, differences in electrical charge, molecular conformation, receptor binding, cellular uptake, and degradation in the extracellular space affect the final distribution of each molecule. Nonetheless, knowledge of the tissue movement of a drug relative to movement of the surrogate tracer (a correlation) permits calculation of the drug distribution from knowledge of the distribution of the surrogate tracer.

The safety of the CT tracer was examined, and no evidence of direct toxicity or immunological reaction in the brains of rats perfused by convection with IPA-HAS was observed. Iopanoic acid has been used for imaging the gallbladder, and was only associated with rare side effects (acute renal insufficiency, acute thrombocytompenia) [see, Berk et al, "Oral cholecystography with iopanoic acid," *N Engl J Med* 290:204-210 (1974); Curradi et al. "Acute thrombocytopenia following oral cholecystography with iopanoic acid," *Clin Toxicol* 18:221-224 (1981)]. Iopanoic acid is known not to be neurotoxic in the clinical setting [see, Rapoport and Levitan, "Neurotoxicity of X-ray contrast media: Relation to lipid solubility and blood-brain barrier permeability," *Am J Roentgenol Radium Ther Nucl Med* 122:186-193 (1974)]. However, sodium iopanoate used in tissue culture at 1 mM caused immediate death of sympathetic ganglia explants, while 0.1 mM caused vacuolization of fibroblasts. No toxicity occurred at 0.01 mM iopanoic acid (Kormano and Hervonen, "Use of tissue culture to examine neurotoxicity of contrast media," *Radiology* 120: 727-729 (1976)). If completely dissociated, the IPA:HSA conjugate used here would have an iopanoic acid concentration of approximately 0.017 mM. However, the amide bond linking the iopanoic acid to albumin is susceptible to degradation only by intracellular processing and, therefore, is not believed to release free iopanoic acid into the parenchyma. The absence of neurotoxicity in the animals perfused with the IPA:HSA conjugate indicates that dissociation of the compound does not occur, or occurs so slowly that it poses no substantial risk of parenchymal toxicity.

The ability to visualize convective distribution and to determine tissue concentration of a tracer in the perfused region greatly enhances the potential usefulness of CED. Analysis of the efficacy and toxicity of treatment using this delivery approach benefits from confirmation that the infusion is localized to the targeted region, and that the concentrations are in the therapeutic, and not the toxic, range. Furthermore, real-time, non-invasive tracking of the infusion volume permits control of infusion substantially only to the region of interest (for example, the target tissue). As demonstrated here, radiographic and magnetic resonance contrast agents, used as surrogate tracers in standard CT and MRI imaging modalities, provide a practical tool for establishing treatment volumes during high-flow microinfusion. The highly linear correlation between Hounsfeld units in CT images and concentration of CT imaging agent in brain tissue standards demonstrates a means for determination of in vivo concentrations from CT images obtained during CED in patients.

Example 3

In this example, CED incorporating the use of an iodine-based surrogate tracer and computed tomographic (CT)-imaging is demonstrated.

Four primates (*Macaca mulatta*) underwent CED of various volumes (total volume of 90 to 150 µl) of iopamidol (777 Da) in the cerebral white matter combined with CT-imaging during and after infusion (up to 5 days post-infusion), as well as quantitative autoradiography (QAR). Clinical observation ($\leq 20$ weeks) and histopathology were used to evaluate safety and toxicity.

Real-time CT-imaging of the tracer during infusion revealed a clearly defined region of perfusion. The volume of distribution (Vd) increased linearly ($R^2=0.97$) with increasing volume of infusion (Vi). The overall Vd:Vi ratio was $4.1 \pm 0.7$ (mean±S.D.). The distribution of infusate was homogeneous. QAR confirmed the accuracy of the imaged distribution for a small (sucrose; 359 Da) and a large (dextran; 70 kDa) molecule. The distribution of infrsate was identifiable up to 72 hours post-infusion. None of the animals had clinical or histopathologic evidence of toxicity.

Real-time, in vivo, CT-imaging of CED using iopamidol appears to be safe, feasible, and suitable for monitoring convective delivery of both small and large molecules.

Example 4

This example describes the preparation and characterization of a tracer comprising a dendrimer conjugated to a metal chelate, and its use in following, in real time and in vivo, CED in the primate brainstem using MRI.

A DAB-Am64-(1B4M-Gd)$_{64}$ dendrimer is synthesized according to the method described in Kobayashi et al., *Cancer Research,* 61: 4966-4970, 2001. A polypropylenimine diamnobutyl (DAB) dendrimer, Generation 5.0 (DAB-Am-64) is obtained from Aldrich Chemical Company (Milwaukee, Wis.). This dendrimer has 64 terminal primary amino groups and a molecular weight of 7,168. The dendrimer is concentrated to 10 mg/ml and diafiltrated against 0.1M phosphate buffer at pH 9. The DAB-Am-64 dendrimer is reacted with a 64-fold excess of 1B4M at 40° C., and the reaction solution is maintained at pH 9 with 1M NaOH over a reaction time of 48 h. An additional, equal amount of 1B4M is added after 24 h as a solid. The preparation is then purified by diafiltration using Centricon 30 (Amicon, Cambridge Mass.).

Approximately 3 mg of DAB-Am-64-(1B4M-Gd)$_{64}$ is mixed with 10 μmol of Gd(III) citrate (Nakarai, Tokyo, Japan) in 0.3M citrate buffer for 2 h at 40° C. Excess Gd(III) in DAB-Am-64-(1B4M)$_{64}$ by diafiltration using Centricon 30 while simultaneously changing the buffer to 0.05 M PBS at pH 7.4.

The toxicity of the Gd-dendrimer conjugate is investigated in rats. Adult male rats (Sprague-Dawley; n=12) weighing between 300 to 400 grams are anesthetized with isoflurane (2%) and placed in a Kopf stereotactic frame. A sagittal incision is made through the scalp to the level of the skull. A burr hole is placed over the right frontal region. A 32-gauge cannula attached to a 25 μl Hamilton syringe filled with the Gd-dendrimer conjugate is stereotactically placed in the right striatum. The coordinates for placement of the cannula tip in the striatum are 0.5 mm anterior to bregma, 2.8 mm right of midline, and 5 mm below the level of the dura.

To distribute the infusate using convection, a non-compliant, gas-tight, infusion apparatus that was described in Example 1 is used. Using this system, 10 μL Gd-albumin is delivered at a rate of 0.5 μL/minute into the striatum.

After the completion of the infusion, the animals are allowed to awaken. They are observed daily for clinical deficits, and euthanized at the end of the observation period (3 to 60 days). Upon euthanization, the brains are immediately removed and frozen at −70° C. The brains are then cut coronally in 20 μm-thick serial sections on a cryostat at −18° to −20° C. Tissue sections are cut through the entire brain. Sections are stained with hematoxylin and eosin, Luxol fast blue and Nissl. Immunohistochemistry for glial fibrillary acidic protein is performed.

The MRI characteristics of the Gd-dendrimer conjugate are investigated in primates. Several adult Rhesus primates (*Macaca mulatta*) undergo CED of the Gd-dendrimer conjugate to the pontine region of the brainstem. After anesthesia has been induced in the animals, they are intubated, and given halothane general endotracheal anesthesia. The animal's temperature, heart rate, oxygen saturation, electrocardiographic responses, and end-tidal PCO$_2$ are monitored. The head of the animal is then secured into a Kopf stereotactic frame. Using sterile technique, a midline skin incision is made from the anterior to the posterior aspect of the vertex of the animal skull. Self-retaining retractors are placed within the wound to expose the underlying skull. A burr hole (1.0 cm) is placed over the stereotactically determined entry point, and underlying dura is then incised. The outer guide cannula (see, FIG. 1; outer diameter 0.027 in.; inner diameter 0.020 in.) is then stereotactically placed through the dural opening along the target trajectory to a level 1.5 cm above the desired pontine target. The outer guide cannula is then secured in place with methylmethacrylate. The inner cannula (see, FIG. 1; outer diameter 0.014 in.; inner diameter 0.006 in.), after being connected to the infusion apparatus, is then placed through the outer guide cannula to the target (see, FIG. 1). The animal is then placed in the MR-scanner for imaging studies during infusion.

Again, to distribute infusate into the brainstem using convection, the non-compliant delivery system that was described above is used. Real-time MRI of the Gd-dendrimer conjugate is performed. After placement of the infusion cannula, coronal T1-weighted MR-images are obtained to determine the precise location of the inner cannula. Once cannula placement is confirmed, infusions are started and T1-weighted MR-images (1.5 Tesla) (slice thickness 1 to 1.5 mm; 0 mm spacing) in 3 planes (sagittal, axial, and coronal) are obtained at approximately 20 to 40 minute intervals until the infusions is complete. MR-images are analyzed on a Sun Workstation. Three-dimensional volumes of distribution (Vd) are calculated using a threshold for segmentation that is the signal intensity value 2 standard deviations above the mean baseline signal for the surrounding non-infused anatomic region. To determine homogeneity of the infusion over the infused Vd, line profiles are obtained through the center of the infusion as seen on coronal images. The validity and accuracy of these methods for calculating Vd and homogeneity from MR-imaging are confirmed using quantitative autoradiography (QAR) as described in Example 2.

Post-infusion imaging is also performed. Several primates undergo MR-imaging on days 0, 1, 2, 4, and 7 days after infusion of the Gd-dendrimer conjugate. T1-weighted MR-images (1.5 Tesla) (slice thickness 1 mm; 0 mm spacing) in 3 planes (sagittal, axial, and coronal) are obtained. Three-dimensional Vd is calculated and homogeneity of the infusion is determined as described previously.

Primates are also observed daily for medical or neurologic difficulties over the study period (18 to 35 days). Each animal undergoes postoperative videotaping within 48 hours of infusion completion and within 24 hours of euthanization.

After sacrifice, the animals' brains are perfused with phosphate buffered saline followed by 10% formalin. The brainstems are then cut coronally in 20-μm thick serial sections. Tissue sections through the entire brainstem are histologically processed, and representative sections from each tissue block are stained with hematoxylin and eosin, Luxol fast blue, and Nissl. Immunohistochemistry for glial fibrillary acidic protein is performed.

Statistical analysis is performed on Stat View 5.0 (Abacus, Berkley Calif.).

Example 5

The presently disclosed method involves delivering a therapeutic agent to a target tissue of a subject by CED and using imaging to follow the delivery. By following the delivery using imaging it is possible to deliver the therapeutic agent to substantially only the target tissue. In general, any therapeutic agent may be delivered according to the method, and the agent may be delivered in a dose that is therapeutically effective.

A therapeutic agent or a composition comprising the therapeutic agent may be administered in any dosage that achieves its intended purpose (a therapeutically effective dose). Amounts and regimens for the administration of the therapeutic molecules can be determined readily by those with ordinary skill in the clinical art of treating diseases. Amounts effective for therapeutic use will, of course, depend on the severity of the disease and the weight and general health state of the patient. Typically, dosages used in vitro may provide useful guidance in the amounts useful for in situ administration of the pharmaceutical composition, and animal models may be used to determine effective dosages for treatment of particular disorders. Various considerations are described, for example, in Gilman et al., eds., *Goodman and Gilman: The Pharmacological Bases of Therapeutics,* 8th ed., Pergamon Press, (1990); and *Remington's Pharmaceutical Sciences,* 17th ed., Mack Publishing Co., Easton, Pa., (1990).

As described above, effective doses of the therapeutic agent will vary depending on the therapeutic agent, the nature and severity of the condition to be treated, the age and condition of the patient and other clinical factors. Thus, the final determination of the appropriate treatment regimen will be made by the attending clinician. Typically, the dose range will be from about 0.1 μg/kg body weight to about 100 mg/kg body weight. Other suitable ranges include doses of from about 1 μg/kg to 10 mg/kg body weight. The concentration of the tracer may be as little as may be detected by MRI and/or CT, or within a range that corresponds to the therapeutic agent dosages given above.

Pharmaceutical preparations may contain only one type of therapeutic molecule, or may be composed of a combination of several types of therapeutic molecules. For CED, formulations usually comprise injectable fluids that include pharmaceutically and physiologically acceptable fluids such as water, physiological saline, balanced salt solutions, aqueous dextrose, glycerol or the like as a vehicle.

Example 6

In addition to treating disorders of the brain, the disclosed CED method may be used to treat other organs. For example, CED followed by imaging may be used to treat abnormalities of the skin, muscles (including the heart), lungs, kidneys, liver, pancreas, prostate, stomach, intestines, colon and sexual organs such as the uterus, testes or ovaries. In one embodiment, heart conditions characterized by an irregular rhythm may be treated by selective ablation of cells responsible for the generation or conduction of aberrant electrical signals. Furthermore, selective treatment of tumors located in any of the organs listed above may be accomplished with the disclosed method, such treatments benefiting from the method's demonstrated ability to deliver therapeutic agents to substantially only the target tissue, which prevents undesired toxic effects in surrounding tissue.

In view of the many possible embodiments to which the principles of our invention may be applied, it should be recognized that the illustrated embodiment is only an example of the invention and should not be taken as a limitation on the scope of the invention. Rather, the scope of the invention is defined by the following claims. We therefore claim as our invention all that comes within the scope and spirit of these claims.

We claim:

1. A method for convection enhanced delivery of a therapeutic agent to a target tissue in a subject's body, comprising:
   providing a solution comprising the therapeutic agent and a tracer;
   delivering the solution to the target tissue by convective interstitial infusion; and
   monitoring a distribution of the solution during delivery by imaging the tracer in the solution.

2. The method of claim 1, further comprising ceasing delivery of the solution to the target tissue when the solution is distributed in a predetermined volume as indicated by the image of the tracer.

3. The method of claim 2, wherein delivery of the solution is delivered substantially only to the target tissue.

4. The method of claim 1, wherein monitoring the distribution of the solution and imaging the tracer comprises performing MRI or CT.

5. The method of claim 4, wherein the tracer comprises a metal chelate of a paramagnetic metal ion.

6. The method of claim 5, wherein the tracer comprises the metal chelate conjugated to the therapeutic agent.

7. The method of claim 6, wherein the tracer comprises the metal chelate conjugated to a carrier molecule.

8. The method of claim 7, wherein the carrier molecule comprises a protein.

9. The method of claim 8, wherein the protein comprises a serum albumin.

10. The method of claim 9, wherein the serum albumin is conjugated to one or more 1B4M chelates of gadolinium (III) ion.

11. The method of claim 7, wherein the carrier molecule comprises a dendrimer.

12. The method of claim 11, wherein the dendrimer is selected from the group consisting of polyalkyelenimine dendrimers and polyamidoamine dendrimers.

13. The method of claim 6, wherein the tracer is chosen to have a mobility in the solid tissue that is substantially similar to the therapeutic agent.

14. The method of claim 4, wherein the tracer comprises an iodinated CT contrast agent.

15. The method of claim 14, wherein the tracer comprises iopanoic acid or iopamidol.

16. The method of claim 1, wherein the tracer comprises an X-ray contrast moiety conjugated to the therapeutic agent.

17. The method of claim 1, wherein the tracer comprises an X-ray contrast agent moiety conjugated to a carrier molecule.

18. The method of claim 17, wherein the carrier molecule comprises a protein.

19. The method of claim 17, wherein the carrier molecule comprises a dendrimer.

20. The method of claim 2, further comprising calculating a correlation between a volume of distribution obtained from the image of the tracer and a volume of distribution for the therapeutic agent, and using the image of the tracer and the correlation to determine whether the therapeutic agent has filled the predetermined volume.

21. The method of claim 1, further comprising detecting undesired flow of the solution and altering the flow if undesired flow is detected.

22. The method of claim 21, wherein the undesired flow comprises backflow along a cannula used to deliver the solution, and further comprising repositioning the cannula or reducing a flow rate used to deliver the solution if backflow is detected.

23. The method of claim 1, wherein delivering the solution comprises infusing the target tissue with the solution at a rate between 0.1 μL/min and 15 μL/min.

24. The method of claim 1, wherein monitoring further comprises measuring a signal intensity of the tracer in the target tissue and using the signal intensity of the tracer to calculate a concentration of the therapeutic agent in the target tissue.

25. The method of claim 1, wherein the target tissue is located in the brain.

26. A method for convection enhanced delivery of a therapeutic agent to substantially only a target tissue, comprising:
- delivering a solution to the target tissue by convective interstitial infusion, the solution comprising the therapeutic agent and a tracer;
- monitoring a distribution of the tracer by MRI or CT as it moves through the target tissue; and
- ceasing delivery of the solution to the target tissue when the distribution of the tracer corresponds to substantially only the target tissue.

27. The method of claim 26, wherein the tracer has a mobility in the target tissue that is substantially similar to the mobility of the therapeutic agent.

28. The method of claim 26, wherein the tracer comprises an imaging moiety, and the imagine moiety is conjugated to the therapeutic agent.

29. The method of claim 26, wherein monitoring further comprises calculating a concentration of the tracer from an image of the tracer and correlating the concentration of the tracer to a concentration of the therapeutic agent delivered to the target tissue.

* * * * *

UNITED STATES PATENT AND TRADEMARK OFFICE
CERTIFICATE OF CORRECTION

PATENT NO. : 7,371,225 B2
APPLICATION NO. : 10/528310
DATED : May 13, 2008
INVENTOR(S) : Oldfield et al.

It is certified that error appears in the above-identified patent and that said Letters Patent is hereby corrected as shown below:

In the Specification:

Column 1, line 66 "microinfision" should be -- microinfusion --.

Column 2, line 65 "only to the" should be -- only the --.

Column 3, line 66 "T1-wieghted" should be -- T1-weighted --.

Column 4, line 23 "gadollnium" should be -- gadolinium --.

Column 5, line 42 "insterstitial" should be -- interstitial --.

Column 5, line 44 "interstial ifusion" should be -- interstitial infusion --.

Column 7, line 44 "immunoglogulins" should be -- immunoglobulins --.

Column 8, line 6 "that that" should be -- that --.

Column 9, line 1 "metals ions" should be -- metal ions --.

Column 9, line 29 "that that" should be -- that --.

Column 9, line 61 "with a surface" should be -- with surface --.

Column 10, line 20 "ioxotriroic" should be -- ioxotrizoic --.

Column 10, line 36 "polyalkyelenimine" should be -- polyalkylenimine --.

Column 11, line 2 "polypropylenimnine" should be -- propylenimine --.

Column 11, line 40 "taargeted" should be -- targeted --.

Column 11, line 47 "mercaptopurne" should be -- mercaptopurine --.

Column 11, line 48 "thiognanine" should be -- thioguanine --.

Column 12, line 13 "Chloroambucil" should be -- Chlorambucil --.

Column 12, line 25 "succininiidyl" should be -- succinimidyl --.

Column 13, line 15 "(4- isothiocyanatobenzyl)" should be -- (4-isothiocyanatobenzyl) --.

Column 13, line 24 "centrifngation" should be -- centrifugation --.

Column 15, line 37 "Berkley" should be -- Berkeley --.

Signed and Sealed this
Twenty-fifth Day of August, 2015

Michelle K. Lee
*Director of the United States Patent and Trademark Office*

CERTIFICATE OF CORRECTION (continued)

Column 16, line 30 "(Fig. 7," should be -- (Fig. 7) --.

Column 18, line 27 "mmnizing" should be -- minimizing --.

Column 19, line 8 "(IP-HSA)" should be -- (IPA-HSA) --.

Column 20, line 37 "2% percent" should be -- 2% --.

Column 22, line 9 "acheived" should be -- achieved --.

Column 22, line 39 "1 µgl/min" should be -- 1 µl/min --.

Column 22, line 42 "astrocytornas" should be -- astrocytomas --.

Column 22, line 60 "(for exaniple," should be -- (for example, --.

Column 23, line 31 "patters" should be -- patterns --.

Column 23, line 32 "drub" should be -- drug --.

Column 23, line 54 "IPA-HAS" should be -- IPA-HSA --.

Column 23, line 57 "thrombocytompenia" should be -- thrombocytopenia --.

Column 24, line 54 "infrsate" should be -- infusate --.

Column 25, line 4 "diamnobutyl" should be -- diaminobutyl --.

Column 25, line 14 "Cambridge MA)." should be -- Cambridge, MA). --.

Column 26, line 16 "infusions is" should be -- infusions are --.

Column 26, line 48 "Berkley CA)." should be -- Berkeley, CA). --.

In the Claims:

Column 28, line 26 "polyalkyelenimine" should be -- polyalkylenimine --.

Column 30, line 5 "imagine" should be -- imaging --.